(12) United States Patent
Combs et al.

(10) Patent No.: US 9,108,984 B2
(45) Date of Patent: Aug. 18, 2015

(54) SUBSTITUTED DIAMINO-PYRIMIDINE AND DIAMINO-PYRIDINE DERIVATIVES AS PI3K INHIBITORS

(75) Inventors: Andrew P. Combs, Kennett Square, PA (US); Yun-Long Li, Chadds Ford, PA (US); Song Mei, Wilmington, DE (US); Eddy W. Yue, Landenberg, PA (US)

(73) Assignees: Incyte Corporation, Wilmington, DE (US); Incyte Holdings Corporation, Wilmington, DE (US)

( * ) Notice: Subject to any disclaimer, the term of this patent is extended or adjusted under 35 U.S.C. 154(b) by 0 days.

(21) Appl. No.: 14/005,120

(22) PCT Filed: Mar. 13, 2012

(86) PCT No.: PCT/US2012/028915
§ 371 (c)(1),
(2), (4) Date: Nov. 8, 2013

(87) PCT Pub. No.: WO2012/125629
PCT Pub. Date: Sep. 20, 2012

(65) Prior Publication Data
US 2014/0066448 A1    Mar. 6, 2014

Related U.S. Application Data

(60) Provisional application No. 61/452,404, filed on Mar. 14, 2011.

(51) Int. Cl.
*A61K 31/498* (2006.01)
*C07D 513/04* (2006.01)
*C07D 403/12* (2006.01)
*C07D 401/12* (2006.01)
*A61K 31/519* (2006.01)

(52) U.S. Cl.
CPC ............ *C07D 513/04* (2013.01); *C07D 403/12* (2013.01); *A61K 31/498* (2013.01); *A61K 31/519* (2013.01); *C07D 401/12* (2013.01)

(58) Field of Classification Search
CPC .. C07D 513/04; C07D 401/12; C07D 403/12; A61K 31/498; A61K 31/519
USPC ........................ 544/235, 278; 514/248, 259.2
See application file for complete search history.

(56) References Cited

U.S. PATENT DOCUMENTS

| | | |
|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmerman |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

Q. Liu et al., 6 Drug Discovery Today: Therapeutic Strategies, 47-55 (2009).*
S.J. Shutteworth et al., 18 Current Medicinal Chemistry, 2686-2714 (2011).*
D. Kong et al., 9 Cancer Science, 1734-1740 (2008).*
L. Zhao et al., 27 Oncogene, 5486-5496 (2008).*
S. Brachmann et al., 21 Current Opinion in Cell Biology, 194-198 (2009).*
J. Engelman et al., 9 Nature Reviews | Cancer, 550-562 (2009).*
D. Courtney et al., 29 Journal of Clinical Oncology, 1075-1083, 1076 (2010).*
A. Ghigo et al., 32 BioEssays, 185-196 (2010).*
N.M. Dagia et al., 298 American Journal of Physiology—Cell Physiology, 929-941 (2010).*

(Continued)

*Primary Examiner* — Alexander R Pagano
(74) *Attorney, Agent, or Firm* — Fish & Richardson P.C.

(57) ABSTRACT

The present invention provides substituted diamino-pyrimidine and substituted diamino-pyridine derivatives of Formula I; wherein X, Y, $R^1$, $R^2$, and Ar are defined herein, that modulate the activity of phosphoinositide 3-kinases (PI3Ks) and are useful in the treatment of diseases related to the activity of PI3Ks including, for example, inflammatory disorders, immune-based disorders, cancer, and other diseases.

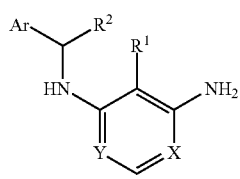

32 Claims, No Drawings

(56) References Cited

U.S. PATENT DOCUMENTS

| | | |
|---|---|---|
| 7,129,264 B2 | 10/2006 | Smallheer et al. |
| 7,494,987 B2 * | 2/2009 | Akada et al. ............. 514/210.01 |
| 7,495,002 B2 | 2/2009 | Langkopf et al. |
| 7,528,143 B2 * | 5/2009 | Noronha et al. ............. 514/275 |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 2003/0008898 A1 | 1/2003 | Mahhoobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikan et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0281884 A1 | 11/2011 | Combs et al. |
| 2011/0312979 A1 | 12/2011 | Li et al. |
| 2012/0157430 A1 | 6/2012 | Li et al. |
| 2013/0029982 A1 | 1/2013 | Castro et al. |
| 2013/0059835 A1 | 3/2013 | Li et al. |
| 2013/0261101 A1 | 10/2013 | Combs et al. |
| 2014/0031355 A1 * | 1/2014 | Fisher et al. ............. 514/248 |
| 2014/0057912 A1 | 2/2014 | Combs et al. |
| 2014/0121222 A1 | 5/2014 | Li et al. |
| 2014/0275127 A1 | 9/2014 | Combs et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011136925 | 7/2011 |
| RU | 2233842 | 8/2004 |
| SU | 1712359 | 2/1992 |
| WO | WO 93/16076 | 8/1993 |
| WO | WO 93/22291 | 11/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |

(56) References Cited

FOREIGN PATENT DOCUMENTS

| | | |
|---|---|---|
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/135009 | 10/2012 |
| WO | WO 2013/033569 | 3/2013 |
| WO | WO 2013/151930 | 10/2013 |

OTHER PUBLICATIONS

E. Hirsch et al., 118 Pharmacology & Therapeutics, 192-205 (2008).*
A Dushianthan et al., 87 Post Graduate Medical Journal, 612-622 (2011).*
N. Kolliputi et al., 297 American Journal of Physiology, Lung Cellular and Molecular Physiology, L6-L16 (2009).*
J. Luo et al., 36 Cell, 823-837 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
Y.S. Yoon et al., 9 The International Journal of Tuberculosis and Lung Disease, 1215-1219 (2005).*
Kinase Inhibitors, Methods in Molecular Biology 795 (B. Kuster ed., 2012).*
U. McDermott et al., 27 Journal of Clinical Oncology, 5650-5659 (2009).*
C.L. Sawyer, Nature, 548-552 (2008).*
C.M. Coughlin et al., Breast Cancer Research Treatment, 1-11 (2010).*
S. Yamada et al., 242 The Journal of Pharmacology and Experimental Therapeutics, 326-330 (1987).*
J. Kim et al., 150 Endocrinology, 3576-3583 (2009).*
"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.
Ali, et al., "Essential role for the p110δ phosphoinositide 3-kinase in the allergic response," Nature. 2004, 431(7011):1007-11.
Allen, et al., "Synthesis of C-6 substituted pyrazolo[1,5-a]pyridines with potent activity against herpesviruses," *Bioorganic & Medicinal Chemistry* (2006), 14(4), 944-954.
Bader, et al., "Cancer-specific mutations in PIK3CA are oncogenic in vivo," Proc Natl Acad Sci U S A. 2006, 103(5):1475-9.
Barber, et al., "PI3Kγ inhibition blocks glomerulonephritis and extends lifespan in a mouse model of systemic lupus," Nat Med. 2005, 11(9):933-5.
Barragan et al., "Protein Kinases in the Regulation of Apoptosis in B-cell Chronic Lymphocytic Leukemia," *Leukemia and Lymphoma*, 2003, 44(11):1865-1870.
Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

(56) References Cited

OTHER PUBLICATIONS

Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.
Bennasar, et al., "Generation and Intermolecular Reactions of 2-Indolylacyl Radicals," *Organic Letters* (2001), 3(11), 1697-1700, CODEN: ORLEF7; ISSN: 1523-7060.
Berge et al., "Pharmaceutical Salts," J Pharma Sci, 1977, 66(1):1-19.
Bergman, et al., "Synthesis of indolocarbazole quinones; potent aryl hydrocarbon receptor ligands," *Tetrahedron* (2002), 58(7), 1443-1452.
Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.
Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Boger, et al., "First and Second Generation Total Synthesis of the Teicoplanin Aglycon," JACS, 123(9), 1862-1871, 2001.
Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," *Bioorganic & Medicinal Chemistry Letters* (2006), 16(17), 4697-4699.
Camps, et al., "Blockade of PI3Kγ suppresses joint inflammation and damage in mouse models of rheumatoid arthritis," Nat Med. 2005, 11(9):936-43.
Cantley, "The Phosphoinositide 3-Kinase Pathway," Science, (2002) 296 (5573):1655-7.
Chai, et al., "Synthesis and in vitro anti-hepatitis B virus activities of some ethyl 6-bromo-5-hydroxy-1H-indole-3-carboxylates,"*Bioorganic & Medicinal Chemistry* (2006), 14(4), 911-917.
Clayton, et al., "A Crucial Role for the p110δ Subunit of Phosphatidylinositol 3-Kinase in B Cell Development and Activation," J Exp Med. 2002, 196(6):753-63.
DeBerardinis et al., "The Biology of Cancer: Metabolic Reprogramming Fuels Cell Growth and Proliferation," Cell Metabolism, Jan. 2008, 7:11-20.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Fadeyeva, et al , "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).
Flinn et al., "Preliminary evidence of clinical activity in a phase I study of CAL-101, a selective inhibitor of the p110δ isoform of phosphatidylinositol 3-kinase (P13K), in patients with select hematologic malignancies," Journal of Clinical Oncology, (abstract), 27(155):3543, 2009.
Floberg et al., "Extractive alkylation of 6-mercaptopurine and determination in plasma by gas chromatography-mass spectrometry," *Journal of Chromatography, Biomedical Applications*, (1981), 225(1), 73-81.
Fruman and Bismuth, "Fine Tuning the Immune Response with P13K," *Immunological Revs.*, 2006, 228:253-272.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota, "Efficient synthesis of 2,9-disubstituted 8-hydroxyadenine derivatives", Organic & Biomolecular Chemistry (2003), 1(8), 1354-1365.
Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of a fluorine-containing cytokinin, N6-pentafluoro-benzyladenosine," *Youji Huaxue* (1988), 8(2), 147-8 (with English abstract).
Ihle et al , "Inhibitors of phosphatidylinositol-3-kinase in cancer therapy", *Molecular Aspects of Medicine*, 31(2):135-144, 2010.
Irie, et al., "Discovery of selective and nonpeptidic cathepsin S inhibitors," *Bioorganic & Medicinal Chemistry Letters* (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie*, International Edition in English (1996), 35(16), 1815-1818.

(56) References Cited

OTHER PUBLICATIONS

Jimenez, et al, "The p85 Regulator Subunit Controls Sequential Activation of Phoshoinositide 3-Kinase by Tyr Kinases and Ras," J Biol Chem., 2002, 277(44):41556-62.

Jou, et al., "Essential, Nonredundant Role for the Phosphoinositide 3-Kinase p110δ in Signaling by the B-Cell Receptor Complex," Mol Cell Biol. 2002, 22(24):8580-91.

Kang et al., "Aplidiamine, a unique zwitterionic benzyl hydroxyadenine from the Western Australian marine ascidian Aplidiopsis sp.," *Tetrahedron Letters* (1997), 38(6), 941-944.

Kang, et al., "Phosphtidylinositol 3-kinase mutations identified in human cancer are oncogenic," Proc Natl Acad Sci U S A. 2005, 102(3):802-7.

Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.

Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.

Kim, et al., "A new structural class of S-adenosylhomocysteine hydrolase inhibitors", Bioorganic & Medicinal Chemistry (2009), 17(18), 6707-6714.

Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.

Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.

Kolasa, et al., "Synthesis of indolylalkoxyiminoalkylcarboxylates as leukotriene biosynthesis inhibitors," *Bioorganic & Medicinal Chemistry* (1997), 5(3), 507-514.

Kong and Yamori, "Advances in Development of Phosphatidylinositol 3-Kinase Inhibitors," Current Medicinal Chemistry, 16:2839-2854, 2009.

Kuduk et al., "Heterocyclic fused pyridone carboxylic acid M1 positive allosteric modulators," *Bioorganic & Medicinal Chemistry Letters* (2010), 20(8), 2533-2537.

Kung et al., "Characterization of a Murine Model of Allergic Pulmonary Inflammation," Int. Arch. Allergy Immunol., (abstract), 105(1):83-90, 1994.

Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.

Kutney, et al., "Dihydropyridines in synthesis and biosynthesis. IV. Dehydrosecodine, in vitro precursor of indole alkaloids," *Canadian Journal of Chemistry* (1982), 60(11), 1269-78.

Lee, et al , "Inhibition of phosphoinositide 3-kinase δ attenuates allergic airway inflammation and hyperresponsiveness in murine asthma model," FASEB J. 2006, 20(3):455-65.

Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Li, et al., "Optimization of the heterocyclic core of the quinazolinone-derived CXCR3 antagonists," *Bioorganic & Medicinal Chemistry Letters* (2008), 18(2), 688-693.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lucas, et al., "Rauwolfia alkaloids. XXXI. The synthesis and activity of some reserpine analogs," *Journal of the American Chemical Society* (1959), 81, 1928-32.

Ma, et al., "Two new constituents from Artemisia capillaris Thunb", Molecules (2008), 13(2), 267-271.

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

Meijer et al., "Treatment of primary Sjögren syndrome with rituximab: extended follow-up, safety and efficacy of retreatment," Ann. Rheum. Dis., 68(2):284-285, 2009.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society, Perkin Transactions 1* (2001), (18), 2213-2216.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+ Br−} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., Generation and behavior of naphthoyloxyl radicals in photocleavage of 1-(naphthoyloxy)-2-pyridones, *Chemistry Letters* (2001), (10), 1064-1065.

(56) References Cited

OTHER PUBLICATIONS

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.
Nettekoven, M., "A combinatorial approach towards 2-acyl-3-amino-indole derivatives," *Tetrahedron Letters* (2000), 41(43), 8251-8254.
Norman, P., "Selective PI3Kδ inhibitors, a review of the patent literature", Expert Opinion on Therapeutic Patents, Informa Healthcare, 21(11):1773-1790, 2011.
Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., "Phosphoinositide 3-kinase δ inhibitor as a novel therapeutic agent in asthma," Respirology, 13:764-771, 2008.
Phillips, et al., "The reaction of anils with 8-quinolinol," *Journal of Organic Chemistry* (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," *Tetrahedron Letters* (2011), 52(4), 512-514.
Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ in inflammatory arthritis and tissue localization of neutrophils," Eur. J. Immunol., 2008, 38(5):1215-24.
Reich, et al., "Preparation of a,b-unsaturated carbonyl compounds and nitriles by selenoxide elimination," *Organic Reactions* (Hoboken, NJ, United States) (1993), 44, No pp. given.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," *Science of Synthesis* (2004), 16, 1155-1267.
Samuels, et al., "High Frequency of Mutations of the PIK3CA Gene in Human Cancers," Science, 2004, 304(5670):554.
Samuels and Ericson, "Oncogenic PI3K and its role in cancer," Curr Opin Oncol., 2006, 18(1):77-82.
Sasaki, et al., "Function of PI3Kγ in Thymocyte Development, T Cell Activation, and Neutrophil Migration," Science, 2000, 287(5455):1040-6.
Saxena, et al., "Pharmacophore-based virtual screening and docking studies on Hsp90 inhibitors", SAR and QSAR in Environmental Research (2010), 21(5-6), 445-462.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Thomas, et al., "Airway inflammation: chemokine-induced neutrophilia and the class I phosphoinositide 3-kinases," Eur J Immunol 2005, 35(4):1283-91.
Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/lh2285/lh2285.pdf.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," J Immunol., 2009, 183:6472-3480.
Xu et al., "Activation of the PI3K/AKT/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidinylinositol 3-Kinase Inhibitor," *J Natl. Cancer Inst.*, 2006, 98(8):545-556.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.

(56) References Cited

OTHER PUBLICATIONS

Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Zhang et al., "Advances in preclinical small molecules for the treatment of NSCLC", Expert Opinion on Therapeutic Patents, 19(6):731-751, 2009.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (7pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
"Angiogenesis" Merriam-Webster.com. Merriam-Webster, n.d. Web Jun. 16, 2014, www.merriam-webster.com/dictionary/angiogenesis, 3 pages.

"Arthritis: MedlinePlus Medical Encyclopedica," 2014, p. 1-5, accessed online Oct. 7, 2014; http://www.nlm.nih.gove/medlineplus/ency/article/001243.htm.
"Autoimmune disorders: MedlinePlus Medical Encyclopedia," 2013, p. 1-4, accessed online Oct. 7, 2014; http://www.nlm.nih.gov/medlineplus/ency/article/000816.htm.
Baek et al., "Complete remission induced by rituximab in refractory, seronegative, muscle-specific, kinase-positive myasthenia gravis," J Neurol Neurosurg Psychiatry, 2007, 78(7):771.
Ball, "PI3K inhibitors as potential therapeutics for autoimmune disease," Drug Discovery Today, 2014, pp. 1195-119.
Cannon, Burger's Medicinal Chemistry and Drug Discovery, Fifth Edition, vol. 1 Principles and Practice, Wiley-Interscience 1995, Ch. 19, pp, 783-803, 784.
Collins et al., "Rituximab treatment of fibrillary glomerulonephritis," Am J Kidney Dis., 2008, 52(6):1158-62.
Crabbe, "The PI3K inhibitor arsenal: choose your weapon!" Trends Biochem Sci., 2007, 32(10):450-56.
Devauchelle-Pensec, "Treatment of Primary Sjogren Syndrome with Rituximab," Annal Internal Med., 2014, 160:233-242.
Lipsky, "Systemic lupus erythematosus: an autoimmune disease of B cell hyperactivity," Nat Immunol., 2001, 2(9):764-6.
Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.
MedicineNet.com [online] "Definition of Cancer," Sep. 18, 2004, retrieved on Sep. 16, 2005. Retrieved from the Internet: http://www.medterms.com, 1 page.
Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.
Segarra et al., "Successful treatment of membranous glomerulonephritis with rituximab in calcineurin inhibitor-dependent patients," Clin J Am Soc Nephrol., 2009, 4(6):1083-8.
Schafer and Kolkhof, "Failure is an option: learning from unsuccessful proof-of-concept trials," Drug Discovery Today, Nov. 2008, 13(21/22):913-916.
WebMD. Lung Disease & Respiratory Health Center: Lung Disease Overview, May 23, 2014, www.webmd.com/lung/lung-diseases-overview, 3 pages.
WebMD. Lung Disease & Respiratory Health Center: ARDS, May 21, 2014, www.webmd.com/lung/ards-acute-respiratory-distress-syndrome?page=2, 4 pages.
WebMD. Osteoarthritis Health Center: Osteoarthritis—prevention, Apr. 9, 2013, www.webmd.com/osteoarthritis/tc/osteoarthritis-prevention, 2 pages.
WebMD. Psoriasis Health Center: Psoriasis—prevention, Jan. 9, 2012, www.webmd.com/skin-problems-and-treatments/psoriasis/psoriasis-prevention, 1 page.
WebMD. Bladder Cancer Health Center: Bladder Cancer-Prevention, Apr. 30, 2013, www.webmd.com/cancer/bladder-cancer/bladder-cancer-prevention, 1 page.
WebMD. Arthritis Health Center: What is Inflammation? Jul. 6, 2012, www.webmd.com/arthritis/about-inflammation?page=2, 4 pages.
International Preliminary Report on Patentability for PCT/US2012/053398, issued Mar. 4, 2014 (6 pgs.).
Office Action in CO Application No. 11-179.464, received on Mar. 14, 2014, 17 pages.
Office Action in JP Application No. 2012-518563, dated Jul. 8, 2014, 6 pages (with English translation).
Delmas and Meunier, "The Management of Paget's Disease of Bone," N Engl J Med., 1997, 336:558-566.
Harley, "Medical Management of Actue Renal Failure," Renal Failure Replacement Therapies, 2008, pp. 26-32.
Hosalkar et al., "Skeletal Trauma and Common Orthopedic Problems," Chpt 10, Khurana (ed.) Bone Pathology, 2009, 93 pages.
Martelli et al., "Targeting the PI3K/AKT/mTOR signaling network in acute myelogenous leukemia," Expert Opin Investig Drugs. Sep. 2009;18(9):1333-49.

\* cited by examiner

SUBSTITUTED DIAMINO-PYRIMIDINE AND DIAMINO-PYRIDINE DERIVATIVES AS PI3K INHIBITORS

This application is a §371 National Stage Application of PCT/US2012/028915, filed Mar. 13, 2012, which claims the benefit of priority of U.S. Provisional Application No. 61/452,404, filed Mar. 14, 2011, which is incorporated herein by reference in its entirety.

FIELD OF THE INVENTION

The present invention provides substituted diamino-pyrimidine and substituted diamino-pyridine derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3): 802-7; Bader, et al., Proc Natl Acad Sci USA. 2006, 103(5): 1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3): 1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44): 5083-90; Mizoguchi, et al., Brain Pathol. 2004, 14(4):372-7; Knobbe, et al., Neuropathol Appl Neurobiol. 2005, 31(5): 486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and others.

SUMMARY

The present invention provides, inter alia, compounds of Formula I:

*[chemical structure of Formula I: Ar-CH(R²)-NH-[ring with R¹, NH₂, X, Y]]* and pharmaceutically acceptable salts thereof; wherein the variables X, Y, R¹, R², and Ar are defined infra.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present invention further provides methods of treating an immune-based disease in a patient, comprising administering to said patient a therapeutically effective amount of a compound of the invention, or a pharmaceutically acceptable salt thereof.

The present invention also provides methods of treating a cancer in a patient, comprising administering to said patient a therapeutically effective amount of a compound of the invention, or a pharmaceutically acceptable salt thereof.

The present invention further provides methods of treating a lung disease in a patient, comprising administering to said patient a therapeutically effective amount of a compound of the invention, or a pharmaceutically acceptable salt thereof.

The present invention also provides a compound of invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

DETAILED DESCRIPTION

The present invention provides, inter alia, a compound of Formula I:

*[chemical structure of Formula I]* or a pharmaceutically acceptable salt thereof; wherein:

X is CH or N;
Y is CH or N;
provided that at least one of X and Y is N;
Ar is

*[two chemical structures: a cinnoline-type ring with R³ and Cy substituents, or a thiazolo-pyrimidinone with R⁴ and Cy substituents]*

$R^1$ is F, CN, $C_{1-3}$ haloalkyl, $C_{1-4}$alkyl-NHC(=O)— or $(C_{1-4}$alkyl$)_2$NC(=O)—;
$R^2$ is methyl or ethyl;
$R^3$ is F, Cl, or methyl;
$R^4$ is Cl or methyl; and
Cy is phenyl or pyridyl, each of which is substituted by 0, 1, or 2 groups independently selected from fluoro and chloro.

In one embodiment, X is N and Y is N.
In one embodiment, $R^1$ is CN.
In one embodiment, $R^2$ is methyl.
In one embodiment, Cy is phenyl or pyridyl, each of which is substituted by 0, 1, or 2 fluoro groups.
In one embodiment, Cy is phenyl, which is substituted by 0, 1, or 2 groups independently selected from fluoro and chloro.
In one embodiment, Cy is phenyl, which is substituted by 0, 1, or 2 fluoro groups.
In one embodiment, Cy is phenyl.
In one embodiment, Cy is 3-fluorophenyl.
In one embodiment, Cy is 2-fluorophenyl.
In one embodiment, Cy is 3,5-difluorophenyl.
In one embodiment, Cy is pyridyl, which is substituted by 0, 1, or 2 groups independently selected from fluoro and chloro.
In one embodiment, Cy is pyridyl, which is substituted by 0 or 1 fluoro group.
In one embodiment, Ar is:

*[chemical structure: cinnoline ring with R³ and Cy]*

In one embodiment, Ar is:

*[chemical structure: thiazolo-pyrimidinone with R⁴ and Cy]*

In some embodiments, $R^3$ is Cl or methyl.
In one embodiment, $R^3$ is Cl.
In one embodiment, $R^3$ is methyl.

In one embodiment, $R^4$ is methyl.

In some embodiments, the compound is a compound of Formula II:

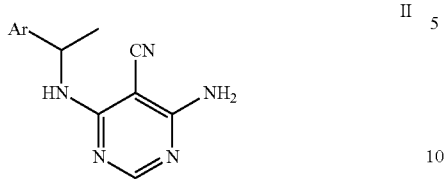

II or a pharmaceutically acceptable salt thereof, wherein:

Ar is:

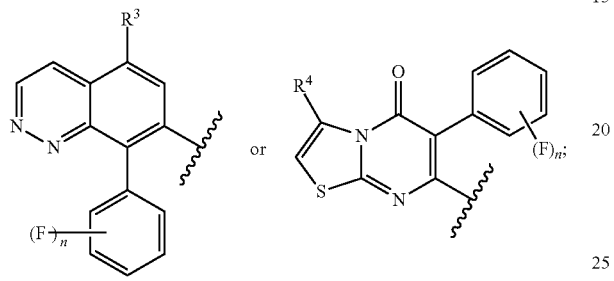

n is 0, 1, or 2; and $R^3$ and $R^4$ are defined as described anywhere herein.

In some embodiments, the compound is a compound of Formula IIIa:

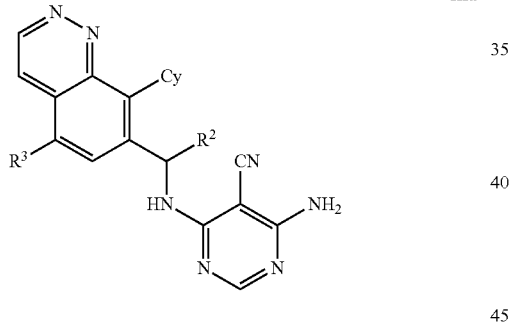

IIIa or a pharmaceutically acceptable salt thereof, wherein $R^2$, $R^3$ and Cy are defined as described anywhere herein.

In some embodiments, the compound is a compound of Formula IIIb:

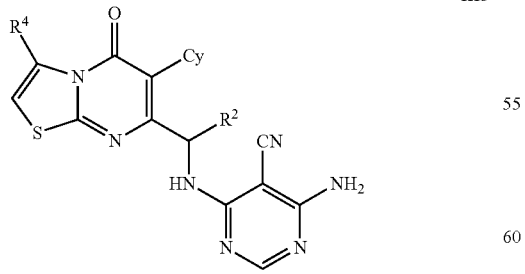

IIIb or a pharmaceutically acceptable salt thereof, wherein $R^2$, $R^4$ and Cy are defined as described anywhere herein.

In some embodiments, the compound is a compound of Formula IVa:

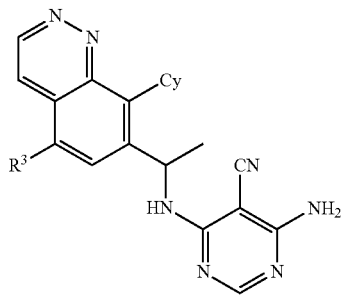

IVa or a pharmaceutically acceptable salt thereof, wherein $R^3$ and Cy are defined as described anywhere herein.

In some embodiments, the compound is a compound of Formula IVb:

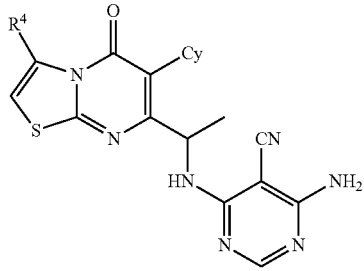

IVb or a pharmaceutically acceptable salt thereof, wherein $R^4$ and Cy are defined as described anywhere herein.

In some embodiments, the compound is a compound of Formula Va:

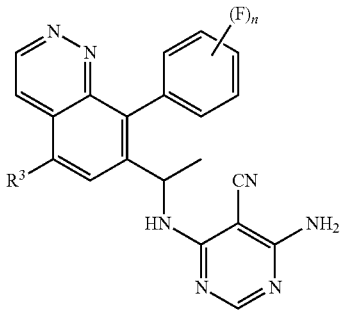

Va or a pharmaceutically acceptable salt thereof, wherein n is 0, 1, or 2; and $R^3$ is defined as described anywhere herein.

In some embodiments, the compound is a compound of Formula Vb:

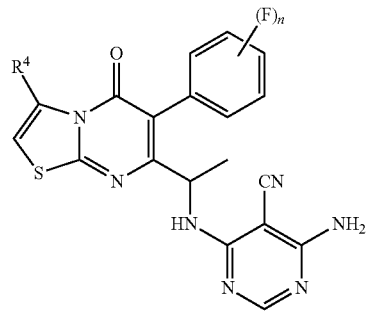

Vb or a pharmaceutically acceptable salt thereof, wherein n is 0, 1, or 2; and $R^4$ is defined as described anywhere herein.

In some embodiments, n is 1 for the compounds of Formulas II, IIIa, IIIb, IVa, IVb, Va, and Vb.

In one embodiment, the compound is 4-amino-6-({1-[5-chloro-8-(3-fluorophenyl)cinnolin-7-yl]ethyl}amino)-pyrimidine-5-carbonitrile, or a pharmaceutically acceptable salt thereof.

In one embodiment, the compound is 4-amino-6-({(1S)-1-[5-chloro-8-(3-fluorophenyl)cinnolin-7-yl]ethyl}amino)-pyrimidine-5-carbonitrile, or a pharmaceutically acceptable salt thereof.

In one embodiment, the compound is 4-amino-6-({1-[6-(3-fluorophenyl)-3-methyl-5-oxo-5H-[1,3]thiazolo[3,2-a]pyrimidin-7-yl]ethyl}amino)pyrimidine-5-carbonitrile, or a pharmaceutically acceptable salt thereof.

In one embodiment, the compound is 4-amino-6-({(1S)-1-[6-(3-fluorophenyl)-3-methyl-5-oxo-5H-[1,3]thiazolo[3,2-a]pyrimidin-7-yl]ethyl}amino)pyrimidine-5-carbonitrile, or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$alkyl", employed alone or in combination with other terms, refers to a saturated hydrocarbon group that may be straight-chain or branched, having n to m carbons. In some embodiments, the alkyl group contains from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, or sec-butyl. As used herein, the term "$C_{n-m}$haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 3 carbon atoms or 1 to 2 carbon atoms. Examples of haloalkyl moieties include, but are not limited to, $CF_3$, $CHF_2$ and $CH_2F$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of a-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification. Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Example synthetic methods for preparing compounds of Formula I, wherein Ar is

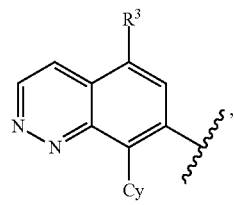

are provided in Scheme I. Cinnoline compounds of Formula I can be synthesized starting from a phenol compound (i) as shown in Scheme I. The phenol compound (i) can be halogenated with N-bromosuccinamide or N-chlorosuccinamide to give compound (ii). The iodo of compound (ii) can be transformed to the alkyne (iii) under Sonagashira coupling conditions. Compound (iii) can be nitrated to give the nitro compound (iv). The phenol of compound (iv) can be converted to a triflate with triflic anhydride and the triflate can be coupled to Cy-M, where M is a boronic acid, boronic ester or an appropriately substituted metal (e.g., Cy-M is Cy-B(OH)$_2$), under standard Suzuki conditions (e.g., in the presence of a palladium(0) catalyst, such as tetrakis(triphenylphosphine) palladium(0) and a base (e.g., a bicarbonate or carbonate base)) to afford compound (v). Compound (v) can be reduced using iron or zinc to give the amine compound (vi). The aniline in compound (vi) can be diazotized and trapped with an amine such as diethylamine or pyrrolidine to give compound (vii). Hydrolysis of compound (vii) to convert the ester to an acid can also remove the TMS group. The acid can then be activated with a coupling agent (e.g. HBTU, HATU) and then reacted with N,O-dimethylhydroxylamine to give a N-methoxy-N-methylcarboxamide derivative (viii). Amide (viii) may then be reacted with a Grignard reagent of formula R$^2$—MgCl to give a ketone (ix). The ketone (ix) can be reduced to give an alcohol and cyclized to the cinnoline under standard thermal conditions or with microwave irradiation to give compound (x). The alcohol of compound (x) can be converted to the mesylate and reacted with sodium azide to give an azide derivative (xi). Optical isomers of the azid derivative (xi) can be optionally separated at this point using suitable separation techniques including column chromatography. The azide group may then be converted to an amine (xii) under appropriate conditions such as trimethylphosphine or trimethylsilyliodide. Finally amine (xii) can be reacted with a halide compound of formula (xiii), wherein X$^1$ is halo (e.g., chloro) to give a cinnoline compound of Formula I.

Scheme I

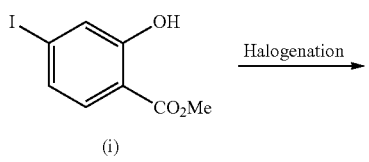

Halogenation

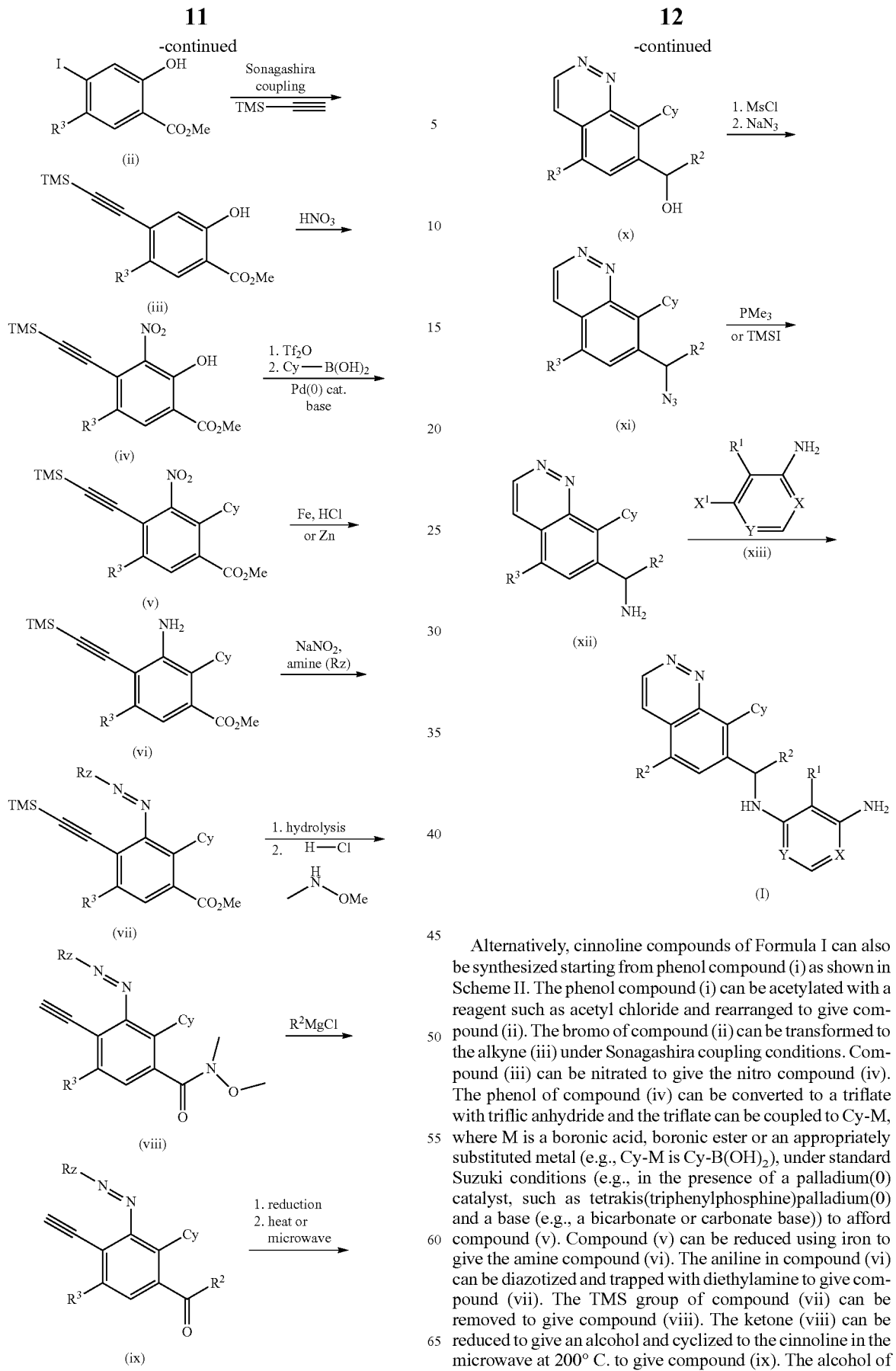

Alternatively, cinnoline compounds of Formula I can also be synthesized starting from phenol compound (i) as shown in Scheme II. The phenol compound (i) can be acetylated with a reagent such as acetyl chloride and rearranged to give compound (ii). The bromo of compound (ii) can be transformed to the alkyne (iii) under Sonagashira coupling conditions. Compound (iii) can be nitrated to give the nitro compound (iv). The phenol of compound (iv) can be converted to a triflate with triflic anhydride and the triflate can be coupled to Cy-M, where M is a boronic acid, boronic ester or an appropriately substituted metal (e.g., Cy-M is Cy-B(OH)$_2$), under standard Suzuki conditions (e.g., in the presence of a palladium(0) catalyst, such as tetrakis(triphenylphosphine)palladium(0) and a base (e.g., a bicarbonate or carbonate base)) to afford compound (v). Compound (v) can be reduced using iron to give the amine compound (vi). The aniline in compound (vi) can be diazotized and trapped with diethylamine to give compound (vii). The TMS group of compound (vii) can be removed to give compound (viii). The ketone (viii) can be reduced to give an alcohol and cyclized to the cinnoline in the microwave at 200° C. to give compound (ix). The alcohol of compound (ix) can be converted to the mesylate and reacted with sodium azide to give an azide derivative (x). The azide group may then be converted to an amine (xi) under appropriate conditions such as trimethylphosphine. Finally, amine (xi) can be reacted with a halide compound of formula (xii) to give a compound of Formula I.

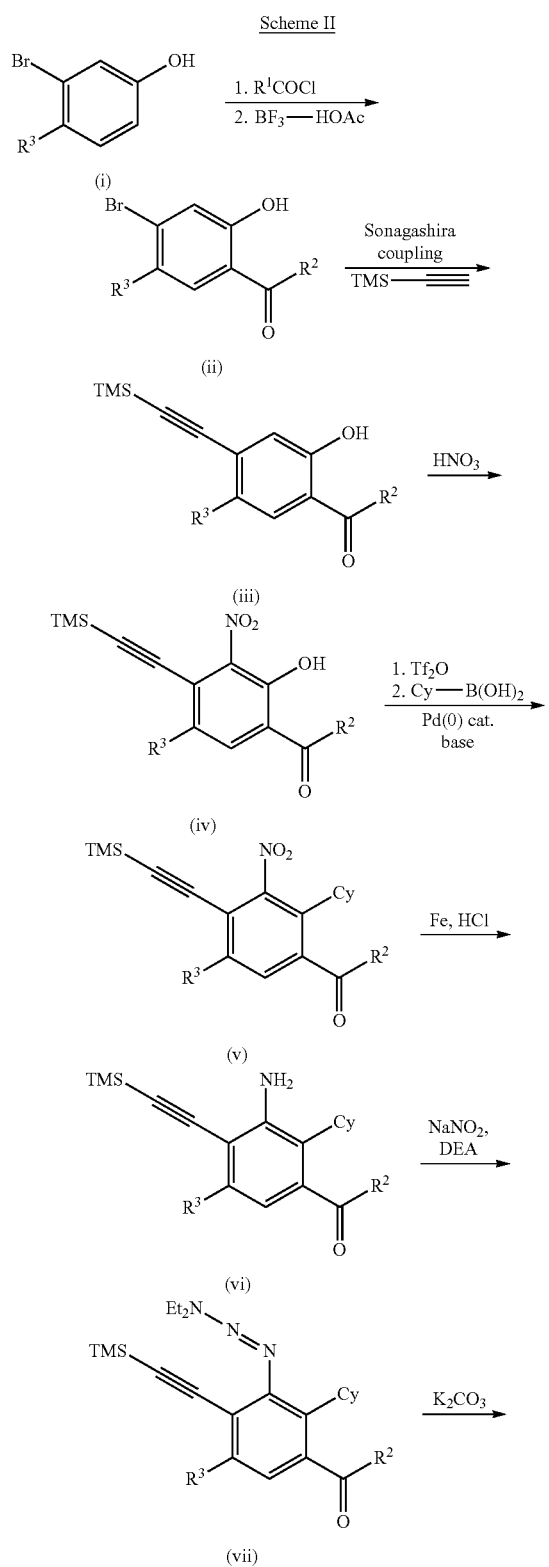

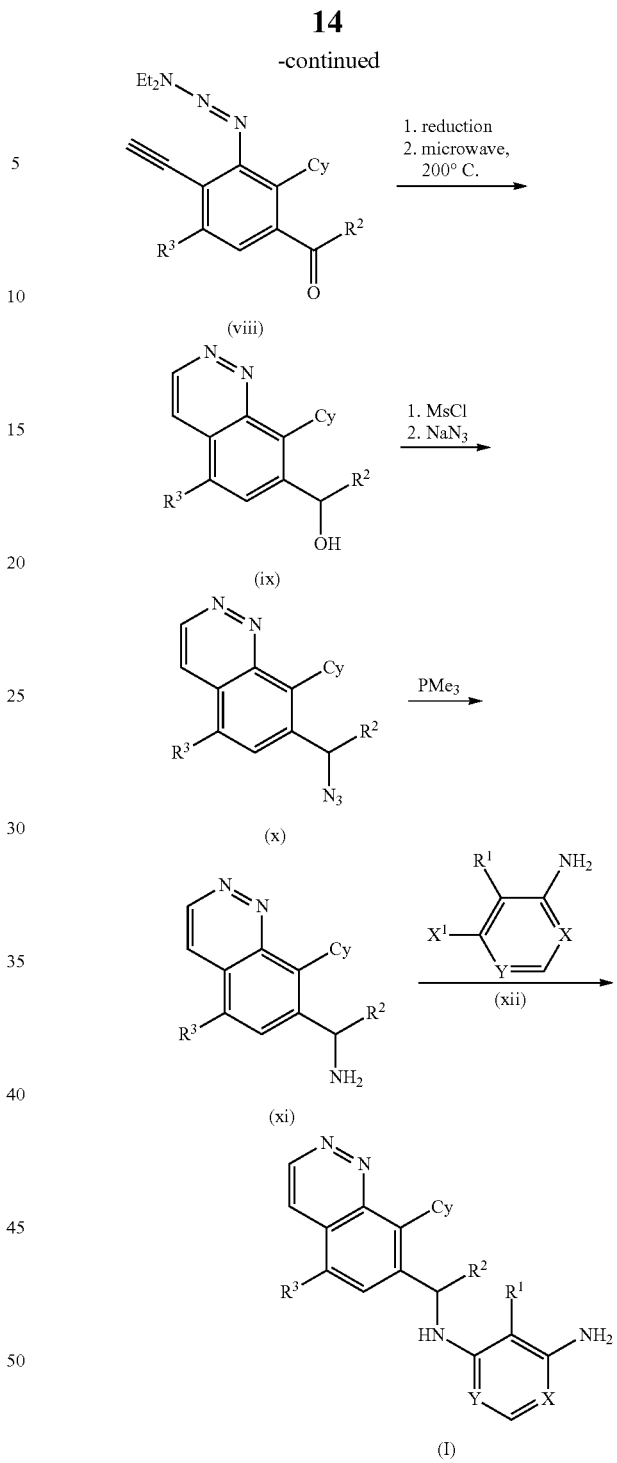

Compounds of Formula I having a 5-oxo-5H-[1,3]thiazolo[3,2-a]pyrimidin-7-yl moiety can be prepared according to the methods described in, e.g., US Pub. No. 2011/0015212, which is incorporated by reference herein in its entirety. The thiazolopyrmidinyl compounds can also be generally prepared according to the procedure outlined in Scheme III shown below. An oxoalkanoic acid ester of formula (i) can be brominated with an appropriate bromination reagent such as $Br_2$ and the brominated product can be combined with a 1,3-thiazol-2-amine derivative of formula (ii) to form a brominealkyl thiazolopyrmidine of formula (iii). The intermediate (iii) can be further brominated with a suitable bromination reagent such as N-bromosuccinimide to form the 6-bromo thiazolopyrimidine of formula (iv). Compound (iv) can be further reacted with an azide derivative (such as sodium azide) to produce the azide intermediate (v) which, in turn, can be reduced to the amine (vi) with a suitable reducing agent (e.g., TMSCl/NaI or H₂ with Pd/C). Optical isomers of the amine derivative (vi) can be optionally separated at this point using suitable separation techniques including column chromatography and/or fractional recrystallizaion using a chiral resolving acid. The amine group of compound (vi) can further be optionally converted to a salt form (v, where X⁻ is an organic or inorganic anion) if needed for facilitating enantiomeric resolution or purification. The salt (vii) (or free base) can be protected with a suitable amino protecting group such as BOC (e.g., by reacting with N-tert-butoxycarbonyl), followed by Suzuki coupling with Cy-B(OH)₂. The Suzuki coupling product can be deprotected to afford the penultimate intermediate (viii). Finally, intermediate (viii) can be reacted with appropriate compound of formula (ix), wherein X¹ is halo (e.g., chloro), to form the 5-oxo-5H-[1,3]thiazolo[3,2-a]pyrimindin-7-yl compounds of Formula I.

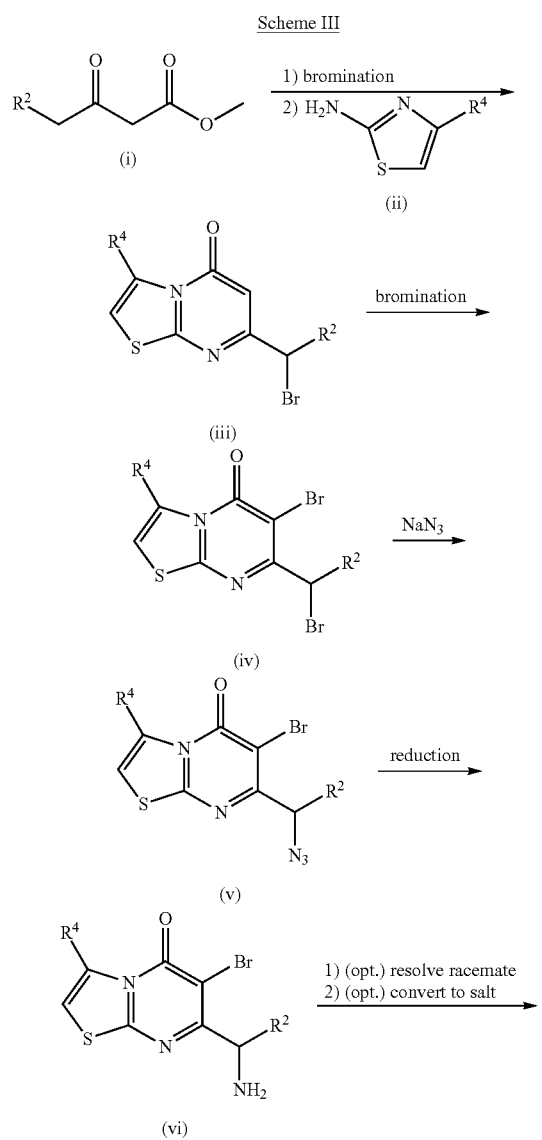

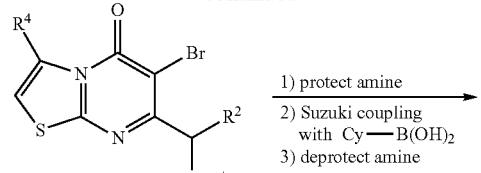

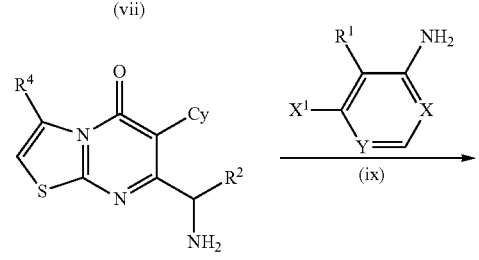

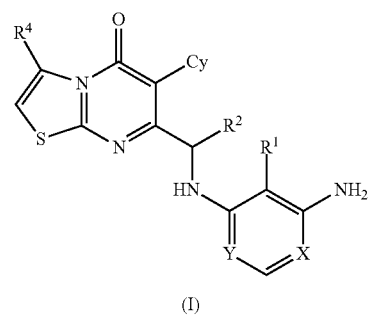

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK, c-MET, VEGFR, PDGFR, cKit, IGF-1R, RAF, FAK, and mTOR kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, and bendamustine (Treanda).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PI3K labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br. In some embodiments, one or more H atoms for any compound described herein is each replaced by a deuterium atom.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified. Where the procedures refer to peak 1 or peak 2, "peak 1" refers to the compound which eluted first, whereas "peak 2" refers to the compound which eluted second.

Example 1

4-Amino-6-({1-[5-chloro-8-(3-fluorophenyl)cinnolin-7-yl]ethyl}amino)-pyrimidine-5-carbonitrile

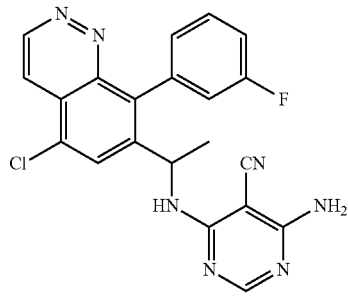 [SMILES: CC(Nc1ncnc(N)c1C#N)c1cc(Cl)c2ccnnc2c1-c1cccc(F)c1]

Step A: Methyl 5-chloro-2-hydroxy-4-iodobenzoate

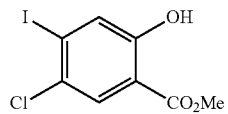

A solution of methyl 2-hydroxy-4-iodobenzoate (50 g, 0.18 mol) [Aldrich, 652636] in acetic acid (360 mL) was treated with N-chlorosuccinimide (29 g, 0.22 mol) and heated at 100° C. for 1 hour. The reaction mixture was cooled until the internal temperature was 19° C. and then the solid that precipitated was filtered, washed with cold acetic acid, and air dried. The solid was diluted with toluene and concentrated (2×200 mL) to remove residual acetic acid to give 34.8 g of the desired product. The filtrate was concentrated, and the residue was purified by flash column chromatography using ethyl acetate in hexanes (0%-20%) to give an additional 8.6 g of desired product (total yield=43 g, 77%). LCMS for $C_8H_7ClIO_3$ (M+H)$^+$: m/z=312.9; Found: 313.0.

Step B: Methyl 5-chloro-2-hydroxy-4-[(trimethylsilyl)ethynyl]benzoate

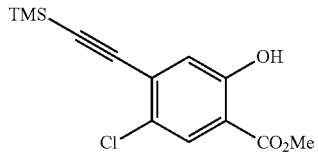 [SMILES: COC(=O)c1cc(Cl)c(C#C[Si](C)(C)C)cc1O]

A solution of copper (I) iodide (1.1 g, 5.8 mmol) in triethylamine (32 mL) was degassed with nitrogen, treated with (trimethylsilyl)acetylene (4.5 mL, 32 mmol), degassed with nitrogen, and stirred at 20° C. for 10 minutes. The reaction mixture was treated with bis(triphenylphosphine)palladium (II) chloride (0.56 g, 0.80 mmol), degassed with nitrogen, and stirred at 20° C. for 30 minutes. The reaction mixture was treated with methyl 5-chloro-2-hydroxy-4-iodobenzoate (5.0 g, 16 mmol), degassed with nitrogen, and stirred at 75° C. for 2 hours. The reaction mixture was filtered over celite, washed with ethyl acetate, and concentrated to a crude residue. Purification via flash column chromatography using ethyl acetate in hexanes (0%-20%) gave the desired product (4.31 g, 95%). LCMS for $C_{13}H_{16}ClO_3Si$ (M+H)$^+$: m/z=283.1; Found: 282.9.

Step C: Methyl 5-chloro-2-hydroxy-3-nitro-4-[(trimethylsilyl)ethynyl]benzoate

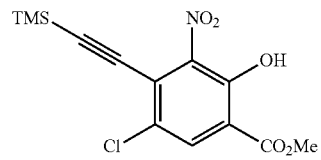 [SMILES: COC(=O)c1cc(Cl)c(C#C[Si](C)(C)C)c([N+](=O)[O-])c1O]

A solution of methyl 5-chloro-2-hydroxy-4-[(trimethylsilyl)ethynyl]benzoate (15 g, 53 mmol) in acetic acid (110 mL) at 55° C. was treated with a solution of nitric acid (7.8 mL, 190 mmol) in acetic acid (7.8 mL, 140 mmol) dropwise and stirred at 55° C. for 30 minutes. The reaction mixture contained only starting material and was treated with an additional solution of nitric acid (2.2 mL, 53 mmol) in acetic acid (2.2 mL, 39 mmol) dropwise and stirred at 55° C. for 1.5 hour. The reaction mixture was cooled to 0° C. and treated with ice followed by cold water. The reaction mixture was stirred until the ice melted, filtered, washed with cold water, and air dried to give the desired product (11.7 g, 67%) as a tan solid. This material was used without further purification. LCMS for $C_{13}H_{15}ClNO_5Si$ (M+H)$^+$: m/z=328.0; Found: 327.8.

Step D: Methyl 5-chloro-3-nitro-2-{[(trisuoromethyl)sulfonyl]oxy}-4-[(trimethylsilyl)ethynyl]benzoate

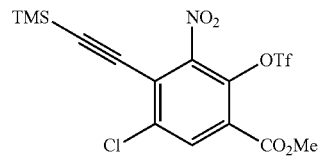 [SMILES: COC(=O)c1cc(Cl)c(C#C[Si](C)(C)C)c([N+](=O)[O-])c1OS(=O)(=O)C(F)(F)F]

A solution of methyl 5-chloro-2-hydroxy-3-nitro-4-[(trimethylsily)ethynyl]benzoate (8.0 g, 24 mmol) in dichloromethane (170 mL) was treated with triethylamine (8.5 mL, 61 mmol), cooled to −10° C., treated with trifluoromethanesulfonic anhydride (8.2 mL, 49 mmol), and stirred at −10° C. for 30 minutes. The reaction mixture was quenched with water, warmed to 20° C., and diluted with dichloromethane. The organic layer was washed with water and brine, dried with sodium sulfate, filtered, and concentrated to a crude residue. The crude material was diluted with dichloromethane and adsorbed onto 50 g of silica gel. Purification by flash column chromatography using ethyl acetate in hexanes (0%-10%) gave the desired product (9.5 g, 85%). LCMS for $C_{14}H_{14}ClF_3NO_7SSi$ (M+H)⁺: m/z=460.0; Found: 459.7.

Step E: Methyl 4-chloro-3'-fluoro-6-nitro-5-[(trimethylsilyl)ethynyl]biphenyl-2-carboxylate

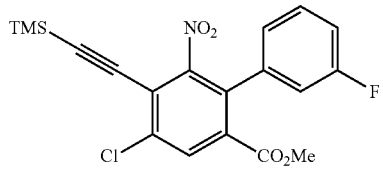 [SMILES: COC(=O)c1cc(Cl)c(C#C[Si](C)(C)C)c([N+](=O)[O-])c1-c1cccc(F)c1]

A solution of methyl 5-chloro-3-nitro-2-{[(trifluoromethyl)sulfonyl]oxy}-4-[(trimethylsilyl)ethynyl]benzoate (9.3 g, 20 mmol) and (3-fluorophenyl)boronic acid (4.3 g, 30 mmol) in toluene (200 mL) was treated with water (200 mL) saturated with sodium bicarbonate (3.4 g, 40 mmol). The reaction mixture was degassed with nitrogen for 10 minutes, treated with tetrakis(triphenylphosphine)palladium(0) (1.2 g, 1.0 mmol), degassed with nitrogen for 10 minutes, and heated at 80° C. for 6 hours. The reaction mixture was cooled to 20° C. and the organic layer was separated. The aqueous layer was extracted with ethyl acetate. The combined organic layers were dried with sodium sulfate, filtered, and concentrated to a crude residue. The crude material was diluted with dichloromethane and adsorbed onto 36 g of silica gel. Purification by flash column chromatography using ethyl acetate in hexanes (0%-40%) gave the desired product (7.1 g, 86%). LCMS for $C_{19}H_{18}ClFNO_4Si$ (M+H)⁺: m/z=406.1; Found: 405.7.

Step F: Methyl 6-amino-4-chloro-3'-fluoro-5-[(trimethylsilyl)ethynyl]biphenyl-2-carboxylate

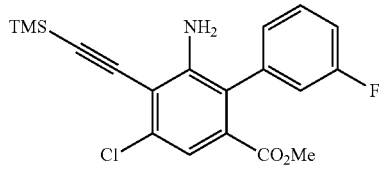

A suspension of iron (<10 micron) (1.6 g, 29 mmol) in methanol (24 mL) was treated with 6 M hydrogen chloride in water (0.4 mL, 2.4 mmol) and heated at 60° C. for 2 hours.

The reaction mixture was treated with 5 M ammonium chloride in water (4.1 mL, 21 mmol) followed by methyl 4-chloro-3'-fluoro-6-nitro-5-[(trimethylsilyl)ethynyl]biphenyl-2-carboxylate (1.9 g, 4.8 mmol) and heated at 60° C. for 16 hours. The reaction mixture was filtered over celite, washed with methanol, and the filtrate was concentrated to a solid. The solid was diluted with ethyl acetate (200 mL) and saturated sodium bicarbonate (100 mL) and stirred for a few minutes. The organic layer was separated, washed with brine, dried with sodium sulfate, filtered, and concentrated to a crude residue. Purification by flash column chromatography using ethyl acetate in hexanes (0%-10%) gave the desired product (1.5 g, 86%). LCMS for $C_{19}H_{20}ClFNO_2Si$ (M+H)⁺: m/z=376.1; Found: 376.1.

Step G: Methyl 4-chloro-6-[(1E)-3,3-diethyltriaz-1-en-1-yl]-3'-fluoro-5-[(trimethylsilyl)ethynyl]biphenyl-2-carboxylate

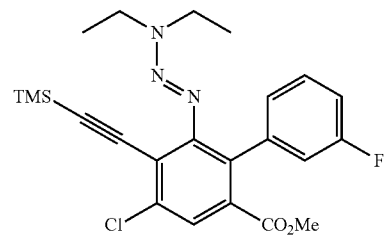 [SMILES: CCN(CC)/N=N/c1c(C#C[Si](C)(C)C)c(Cl)cc(C(=O)OC)c1-c1cccc(F)c1]

A solution of methyl 6-amino-4-chloro-3'-fluoro-5-[(trimethylsilyl)ethynyl]biphenyl-2-carboxylate (3.2 g, 8.4 mmol) in tetrahydrofuran (8.1 mL), acetonitrile (8.1 mL), and water (9.3 mL) was cooled to −5° C. and treated with 12 M of hydrogen chloride in water (5.6 mL, 68 mmol) dropwise followed by a solution of sodium nitrite (1.2 g, 17 mmol) in water (6.3 mL)/acetonitrile (2.1 mL) and stirred at −5° C. for 30 minutes. This mixture was added to a solution of diethylamine (8.7 mL, 84 mmol) and potassium carbonate (7.0 g, 51 mmol) in water (76 mL)/acetonitrile (25 mL) that was cooled at 0° C. The reaction mixture was stirred at 0° C. for 30 minutes and warmed to 20° C. The reaction mixture was diluted with saturated sodium bicarbonate (100 mL) and extracted with ethyl acetate (200 mL). The organic layer was separated, washed with brine, dried with sodium sulfate, filtered, and concentrated to a crude oil. Purification by flash column chromatography using dichloromethane in hexanes (0%-50%) gave the desired product (3.3 g, 86%). LCMS for $C_{23}H_{28}ClFN_3O_2Si$ (M+H)⁺: m/z=460.2; Found: 459.8.

Step H: 4-Chloro-6-[(1E)-3,3-diethyltriaz-1-en-1-yl]-5-ethynyl-3'-fluorobiphenyl-2-carboxylic acid

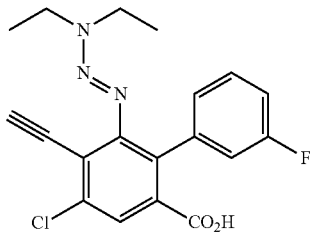 [SMILES: C#Cc1c(Cl)cc(C(=O)O)c(-c2cccc(F)c2)c1/N=N/N(CC)CC]

A solution of methyl 4-chloro-6-[(1E)-3,3-diethyltriaz-1-en-1-yl]-3'-fluoro-5-[(trimethylsilyl)ethynyl]biphenyl-2-carboxylate (3.3 g, 7.1 mmol) in methanol (11 mL) and tetrahydrofuran (11 mL) was treated with 1 M sodium hydroxide in water (29 mL, 29 mmol) dropwise and heated at 65° C. for 1 hour. The reaction mixture was cooled to 0° C. and treated with 3 M hydrogen chloride in water (12 mL, 36 mmol) dropwise. This mixture was poured into 1 M hydrogen chloride in water (100 mL) and extracted with ethyl acetate (2×100 mL). The combined organic extracts were washed with brine (50 mL), dried with sodium sulfate, filtered, and concentrated to give the desired product (quantitative). This material was used without further purification. LCMS for $C_{19}H_{18}ClFN_3O_2$ (M+H)$^+$: m/z=374.1; Found: 373.9.

Step I: 4-Chloro-6-[(1E)-3,3-diethyltriaz-1-en-1-yl]-5-ethynyl-3'-fluoro-N-methoxy-N-methylbiphenyl-2-carboxamide

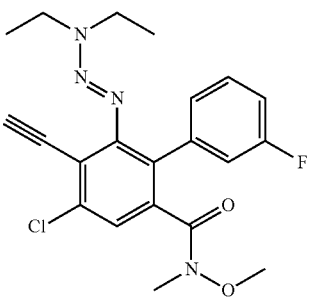 [SMILES: C#Cc1c(Cl)cc(C(=O)N(C)OC)c(-c2cccc(F)c2)c1/N=N/N(CC)CC]

A solution of 4-chloro-6-[(1E)-3,3-diethyltriaz-1-en-1-yl]-5-ethynyl-3'-fluorobiphenyl-2-carboxylic acid (2.7 g, 7.1 mmol) in N,N-dimethylformamide (14 mL) was treated with N,N-diisopropylethylamine (4.3 mL, 25 mmol) followed by O-(benzotriazol-1-yl)-N,N,N',N'-tetramethyluronium hexafluorophosphate (3.5 g, 9.3 mmol) and stirred at 20° C. for 5 minutes. The reaction mixture was treated with N,O-dimethylhydroxylamine hydrochloride (0.9 g, 9.3 mmol) and stirred at 20° C. for 1 hour. The reaction mixture was poured into 0.5 M hydrogen chloride in water (100 mL) and extracted with ethyl acetate (150 mL). The organic layer was washed with saturated sodium bicarbonate (50 mL), brine (25 mL), dried with sodium sulfate, filtered, and concentrated to a crude residue. Purification by flash column chromatography using ethyl acetate in hexanes (0% - 40%) gave the desired product (2.7 g, 92% for 2 steps). LCMS for $C_{21}H_{23}ClFN_4O_2$ (M+H)$^+$: m/z=417.1; Found: 417.0.

Step J: 1-{4-Chloro-6-[(1E)-3,3-diethyltriaz-1-en-1-yl]-5-ethynyl-3'-fluorobiphenyl-2-yl}ethanone

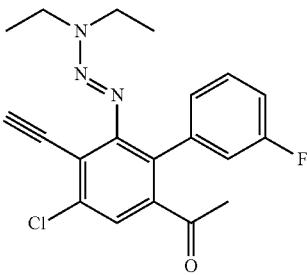 [SMILES: C#Cc1c(Cl)cc(C(C)=O)c(-c2cccc(F)c2)c1/N=N/N(CC)CC]

A solution of 4-chloro-6-[(1E)-3,3-diethyltriaz-1-en-1-yl]-5-ethynyl-3'-fluoro-N-methoxy-N-methylbiphenyl-2-carboxamide (2.7 g, 6.6 mmol) in tetrahydrofuran (26 mL) at 0° C. was treated with 3 M of methylmagnesium chloride in tetrahydrofuran (6.6 mL, 20 mmol) dropwise and stirred at 20° C. for 1 hour. The reaction mixture still contained some starting material and was, therefore, cooled to 0° C., treated with additional 3 M of methylmagnesium chloride in tetrahydrofuran (2.2 mL, 6.6 mmol) dropwise, and stirred at 20° C. for 2 hours. The reaction mixture was cooled to 0° C., quenched with 1 M hydrogen chloride in water (26 mL, 26 mmol), poured into 0.1 M hydrogen chloride in water (100 mL) and extracted with ethyl acetate (150 mL). The organic layer was separated, washed with saturated sodium bicarbonate and brine, dried with sodium sulfate, filtered, and concentrated to give a crude oil. Purification by flash column chromatography using ethyl acetate in hexanes (0% - 20%) gave the desired product (2.3 g, 93%). LCMS for $C_{20}H_{20}ClFN_3O$ (M+H)$^+$: m/z=372.1; Found: 371.9.

Step K: 1-{4-Chloro-6-[(1E)-3,3-diethyltriaz-1-en-1-yl]-5-ethynyl-3'-fluorobiphenyl-2-yl}ethanol

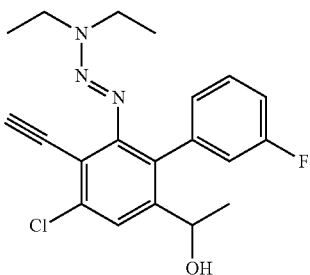 [SMILES: C#Cc1c(Cl)cc(C(C)O)c(-c2cccc(F)c2)c1/N=N/N(CC)CC]

A solution of 1-{4-chloro-6-[(1E)-3,3-diethyltriaz-1-en-1-yl]-5-ethynyl-3'-fluorobiphenyl-2-yl}ethanone (2.3 g, 6.1 mmol) in methanol (38 mL) at 0° C. was treated with sodium borohydride (0.46 g, 12 mmol) in two portions and stirred at 0° C. for 30 minutes. The reaction mixture was quenched with water at 0° C., poured into saturated sodium bicarbonate (50 mL), and extracted with ethyl acetate (2×100 mL). The combined organic extracts were washed with brine (50 mL), dried with sodium sulfate, filtered, and concentrated to give the desired product (quantitative). This material was used without further purification. LCMS for $C_{20}H_{22}ClFN_3O$ (M+H)$^+$: m/z=374.1; Found: 373.9.

Step L: 1-[5-Chloro-8-(3-fluorophenyl)cinnolin-7-yl]ethanol

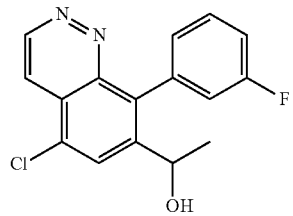 [SMILES: CC(O)c1cc(Cl)c2ccnnc2c1-c1cccc(F)c1]

A solution of 1-{4-chloro-6-[(1E)-3,3-diethyltriaz-1-en-1-yl]-5-ethynyl-3'-fluorobiphenyl-2-yl}ethanol (2.3 g, 6.1 mmol) in 1,2-dichlorobenzene (59 mL) was heated in the microwave at 200° C. for 15 minutes. The reaction mixture was concentrated to give a black residue. Purification by flash column chromatography using acetonitrile in dichloromethane (0%-30%) gave the desired product (1.4 g, 74% for 2 steps). LCMS for $C_{16}H_{13}ClFN_2O$ (M+H)+: m/z=303.1; Found: 302.9.

Step M: 7-(1-Azidoethyl)-5-chloro-8-(3-fluorophenyl)cinnoline

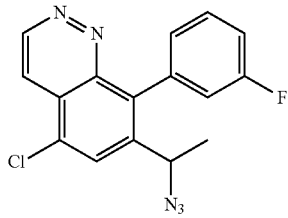 [SMILES: CC(N=[N+]=[N-])c1cc(Cl)c2ccnnc2c1-c1cccc(F)c1]

A solution of 1-[5-chloro-8-(3-fluorophenyecinnolin-7-yl]ethanol (1.4 g, 4.5 mmol) in dichloromethane (22 mL) at -5° C. was treated with N,N-diisopropylethylamine (1.2 mL, 7.1 mmol) followed by methanesulfonyl chloride (0.52 mL, 6.7 mmol) and stirred at −5° C. for 30 minutes. The reaction mixture was quenched with water (100 mL) and extracted with dichloromethane (100 mL). The organic layer was separated, dried with sodium sulfate, filtered, and concentrated to give the intermediate mesylate which was used without further purification. A solution of the mesylate in N,N-dimethylformamide (11 mL) was treated with sodium azide (0.87 g, 13 mmol) and heated at 60° C. for 30 minutes. The reaction mixture was diluted with ethyl acetate (200 mL), washed with solution of saturated sodium bicarbonate (50 mL)/water (50 mL) and brine, dried with sodium sulfate, filtered, and concentrated to give the crude azide. Purification by flash column chromatography using ethyl acetate in hexanes (0%-30%) gave the desired product (1.3 g, 91%). LCMS for $C_{16}H_{12}ClFN_5$ (M+H)+: m/z=328.1; Found: 327.9.

Step N: Chiral separation of 7-(1-azidoethyl)-5-chloro-8-(3-fluorophenyl)cinnoline

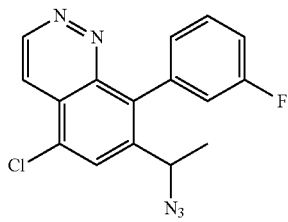 [SMILES: CC(N=[N+]=[N-])c1cc(Cl)c2ccnnc2c1-c1cccc(F)c1]

The racemic mixture of 7-(1-azidoethyl)-5-chloro-8-(3-fluorophenyl)cinnoline was separated by HPLC (Chiracel OD-H, eluting with 10% ethanol/90% hexanes, at flow rate of 20 mL/minute for 13 minutes) to give the two individual enantiomers (retention time (rt)=3.58 minutes, 6.14 minutes). The first peak (rt=3.58 minutes) that eluted off the column was designated peak 1 and the second peak (rt=6.14 minutes) that eluted off the column was designated peak 2.

Step O: Single enantiomer of 1-[5-Chloro-8-(3-fluorophenyl)cinnolin-7-yl]ethanamine (from peak 1)

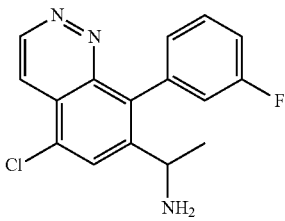

A solution of peak 1 of 7-(1-azidoethyl)-5-chloro-8-(3-fluorophenyl)cinnoline (0.57 g, 1.7 mmol) from step N, in tetrahydrofuran (9.3 mL) and water (1.8 mL) was treated with 1 M of trimethylphosphine in tetrahydrofuran (2.1 mL, 2.1 mmol) and stirred at 20° C. for 30 minutes. The reaction mixture was diluted with ethyl acetate, washed with brine, dried with sodium sulfate, filtered, and concentrated to give the desired product (quantitative). This material was used without further purification. LCMS for $C_{16}H_{14}ClFN_3$ (M+H)+: m/z=302.1; Found: 301.9.

Step P: 4-Amino-6-({1-[5-chloro-8-(3-fluorophenyl)cinnolin-7-yl]ethyl}amino)pyrimidine-5-carbonitrile A solution of the single enantiomer of 1-[5-chloro-8-(3-fluorophenyl)cinnolin-7-yl]ethanamine (400 mg, 1.3 mmol) from step O, 4-amino-6-chloropyrimidine-5-carbonitrile (250 mg, 1.6 mmol), and N,N-diisopropylethylamine (0.69 mL, 4 mmol) in 1-butanol (13 mL) was heated at 120° C. for 3 hours. The reaction mixture was concentrated and the residue was purified by RP-HPLC (XBridge C18 column, eluting with a gradient of acetonitrile/water containing 0.05% TFA, at flow rate of 60 mL/min). The pure fractions were concentrated to remove all of the acetonitrile and the remaining aqueous solution was saturated with sodium bicarbonate. The aqueous solution was extracted with ethyl acetate (300 mL). The organic layer was separated, washed with brine, dried with sodium sulfate, filtered, and concentrated to give a solid. This solid was treated with acetonitrile and concentrated (2×) to give the desired product (0.25 g, 44%). LCMS for $C_{21}H_{16}ClFN_7$ (M+H)+: m/z=420.1; Found: 420.1. $^1$H NMR (300 MHz, DMSO-d$_6$): δ 9.48 (d, J=6.0 Hz, 1 H), 8.44 (d, J=7.8 Hz, 1 H), 8.28 (d, J=6.0 Hz, 1 H), 7.87 - 7.81 (m, 2 H), 7.61 - 7.44 (m, 2 H), 7.34 - 7.17 (m, 4 H), 5.24-5.11 (m, 1 H), 1.43 (d, J=7.0 Hz, 3 H).

Example 2

4-amino-6-({(1S)-1-[6-(3-fluorophenyl)-3-methyl-5-oxo-5H-[1,3]thiazolo[3,2-a]pyrimidin-7-yl]ethyl}amino)pyrimidine-5-carbonitrile

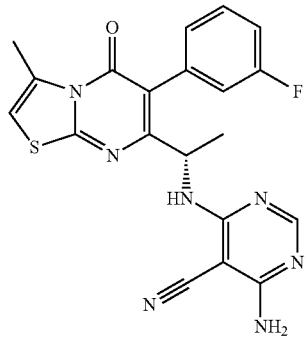 [SMILES: Cc1csc2nc([C@H](C)Nc3ncnc(N)c3C#N)c(-c3cccc(F)c3)c(=O)n12]

Step 1. 7-(1-Bromoethyl)-3-methyl-5H-thiazolo[3,2-a]pyrimidin-5-one

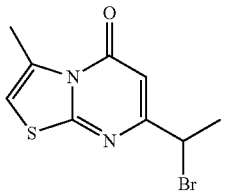

A solution of 3-oxopentanoic acid methyl ester (12.5 g, 96.0 mmol) in methylene chloride (50 mL) was cooled with an ice water bath. The outlet of the flask was attached to a NaOH trap. Bromine (5.19 mL, 101 mmol) in methylene chloride (10 mL, 200 mmol) was added dropwise over a 20-min period, and the reaction mixture was allowed to warm to room temperature and then stirred overnight. The reaction mixture was bubbled with nitrogen for 30 min and then concentrated to give an oil. This oil was used in the next step without further purification. $^1$H NMR (400 MHz, DMSO-$d_6$) δ 4.89 (q, J=6.9 Hz, 1H), 3.85 (s, 2H), 3.63 (s, 3H), 1.64 (d, J=6.7 Hz, 3H).

Into a 3-neck flask fitted with a condenser, a thermometer, and a nitrogen inlet was added polyphosphoric acid (50.0 g, 458 mmol). The flask was heated to ~70° C. to give a liquid that was easy to stir. 4-Methyl-1,3-thiazol-2-amine (10.0 g, 87.6 mmol) was added in small portions with stirring. The internal temperature slowly increased to 78° C. upon mixing. The crude oil obtained above was then added to the flask via a pipette and the mixture was heated to 110° C. under nitrogen. After 6 h of heating, HPLC indicated that the reaction was complete.

The reaction mixture was cooled to ~35° C. Water (70 mL) and EtOAc (200 mL) were added. The mixture was stirred until all solids dissolved. The organic layer was separated. The aqueous layer was extracted with EtOAc (200 mL×2). The combined organic extracts were washed with 1 N aqueous HCl (40 mL×2) with sat. NaHCO$_3$ (50 mL×2) and brine (30 mL). The organic layer was dried and concentrated to give 7-(1-bromoethyl)-3-methyl-5H-thiazolo[3,2-a]pyrimidin-5-one as a yellow solid (11.8 g, 49.3%). LCMS calculated for C$_9$H$_{10}$BrN$_2$OS (M+H)$^+$: m/z 274.96, 272.96; Found: 274.75, 272.75. $^1$H NMR (400 MHz, DMSO-$d_6$) δ 7.05 (m, 1H), 6.27 (s, 1H), 5.17 (q, J=6.9 Hz, 1H), 2.65 (s, 3H), 1.85 (d, J=6.9 Hz, 3H).

Step 2. 6-Bromo-7-(1-bromoethyl)-3-methyl-5H-thiazolo[3,2-a]pyrimidin-5-one

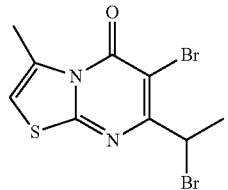

Under nitrogen, a suspension of 7-(1-bromoethyl)-3-methyl-5H-[1,3]thiazolo[3,2-a]pyrimidin-5-one (13.2 g, 48.3 mmol) in acetonitrile (100 mL, 2000 mmol) was stirred until a clear solution was obtained. N-Bromosuccinimide (9.891 g, 55.57 mmol) was then added and the reaction mixture was stirred at 50° C. After 20 minutes, HPLC indicated that the reaction was complete. A solution of sodium sulfite (3.046 g, 24.16 mmol) in water (50 mL) was added and the mixture was stirred at room temperature for 20 minutes. Water (200 mL) was added slowly and the mixture stirred at room temperature for 30 minutes and then filtered. The solid was washed with water (100 mL×3) and dried to give 6-bromo-7-(1-bromoethyl)-3-methyl-5H-thiazolo[3,2-a]pyrimidin-5-one as an off-white solid (15.61 g, 91%). LCMS calculated for C$_9$H$_9$Br$_2$N$_2$OS (M+H)$^+$: m/z 352.87, 354.87; Found: 352.65, 354.60. $^1$H NMR (400 MHz, DMSO-$d_6$) δ 7.15 (q, J=1.3 Hz, 1H), 5.51 (q, J=6.7 Hz, 1H), 2.66 (d, J=1.2 Hz, 3H), 1.90 (d, J=6.7 Hz, 3H).

Step 3. 7-(1-Azidoethyl)-6-bromo-3-methyl-5H-thiazolo[3,2-a]pyrimidin-5-one

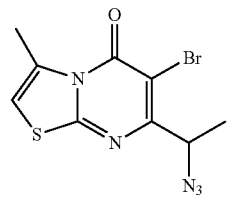 [SMILES: Cc1csc2nc(C(C)N=[N+]=[N-])c(Br)c(=O)n12]

To a suspension of 6-bromo-7-(1-bromoethyl)-3-methyl-5H-[1,3]thiazolo[3,2-a]pyrimidin-5-one (6.85 g, 19.4 mmol) in N,N-dimethylformamide (30.1 mL) was added sodium azide (1.45 g, 22.4 mmol). The mixture slowly turned clear after 5-10 minutes. After 50 minutes, a solution of sodium bicarbonate (4.7 g, 56 mmol) in water (90 mL) was added dropwise with stirring. The mixture was stirred at room temperature for 1 hour and the solid precipitates were filtered off. The solid was then washed with water (30 mL×3), and dried to give 7-(1-azidoethyl)-6-bromo-3-methyl-5H-thiazolo[3,2-a]pyrimidin-5-one as an off-white solid (5.94 g, 97.2%). LCMS calculated for C$_9$H$_9$BrN$_5$OS (M+H)$^+$: m/z 313.96, 315.96; Found: 313.75, 315.75. $^1$H NMR (400 MHz, DMSO-$d_6$) δ 7.15 (q, J=1.3 Hz, 1H), 4.83 (q, J=6.8 Hz, 1H), 2.67 (d, J=1.4 Hz, 3H), 1.48 (d, J=6.8 Hz, 3H).

Step 4. 7-(1-Aminoethyl)-6-bromo-3-methyl-5H-thiazolo[3,2-a]pyrimidin-5-one

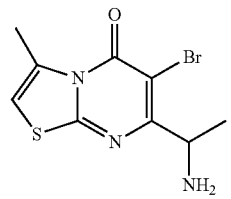

7-(1-Azidoethyl)-6-bromo-3-methyl-5H-thiazolo[3,2-a]pyrimidin-5-one (22.6 g, 71.9 mmol) was mixed with methanol (200 mL). Sodium iodide (64.7 g, 432 mmol) was added and stirred at room temperature for 10 minutes. Chlorotrimethylsilane (54.8 mL, 432 mmol) was dissolved in methanol (29.1 mL) and added dropwise over 10 minutes at 5-25° C. The reaction mixture was stirred at room temperature for 10 minutes. HPLC and TLC showed that the reaction was complete. The reaction was quenched by addition of a solution of sodium thiosulfate (69.4 g, 439 mmol) in water (259 ml) while maintaining the batch temperature at 5-25° C. A large amount of solid was formed, and the pH of the mixture was 3. The mixture was stirred at 0-5° C. for 30 minutes. The pH was adjusted to 11 using 3 N aqueous sodium hydroxide (85 mL).

In order to facilitate product purification and isolation, the N-Boc derivative of the product was prepared. To the mixture was added di-t-butyldicarbonate (28.3 g, 129 mmol) and the reaction mixture was stirred at room temperature for 2 hours. HPLC indicated a small amount of amine remained unreacted. Additional di-t-butyldicarbonate (10.0 g, 45.8 mmol) was added followed by 3 N aqueous sodium hydroxide (15 mL) to adjust the pH to 11. The reaction mixture was stirred at room temperature for 30 minutes. The reaction mixture was extracted with ethyl acetate (150 mL×3). The organic solution which contained the N-Boc derivative of the product was dried over anhydrous sodium sulfate, filtered, and concentrated under reduced pressure to give a residue. The residue was added to a 4 M solution of hydrogen chloride in 1,4-dioxane (206 mL, 824 mmol) and stirred at room temperature for 1.5 hours. HPLC indicated the N-Boc-deprotection was complete. The hydrochloride salt of the product was isolated by filtration, the solid washed with MTBE, dried by suction filtration for 1 hour to give 7-(1-aminoethyl)-6-bromo-3-methyl-5H-thiazolo[3,2-a]pyrimidin-5-one hydrochloride salt (25.1 g) as a purple powder.

The hydrochloride salt was dissolved in water (50 mL) and a 50% solution of sodium hydroxide (about 5 mL) was added to adjust the pH to 11. The mixture was stirred at room temperature for 20 min. The product precipitated and was isolated by filtration. The wet solid was washed with water (10 mL) and dried on the filter under vacuum for 18 hours to give 7-(1-aminoethyl)-6-bromo-3-methyl-5H-thiazolo[3,2-a]pyrimidin-5-one (18.8 g, 65.2 mmol, 90.7% yield) as a yellow powder. LCMS calculated for $C_9H_{11}BrN_3OS$ $(M+H)^+$: m/z 287.97, 289.97; Found: 287.75, 289.75. $^1$H NMR (400 MHz, DMSO-$d_6$) 7.08 (q, J=1.3 Hz, 1H), 4.19 (q, J=6.7 Hz, 1H), 2.65 (d, J=1.3 Hz, 3H), 1.17 (d, J=6.7 Hz, 3H).

Step 5. (S)-1-(6-bromo-3-methyl-5-oxo-5H-thiazolo[3,2-a]pyrimidin-7-yl)ethanaminium (S)-2-hydroxy-2-phenylacetate

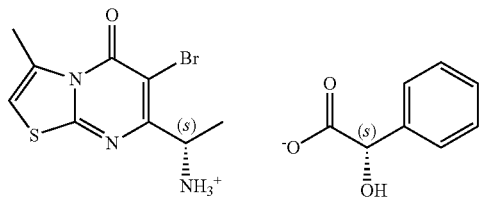

7-(1-Aminoethyl)-6-bromo-3-methyl-5H-thiazolo[3,2-a]pyrimidin-5-one (18.8 g, 65.2 mmol) was dissolved in isopropanol (375 mL) at reflux and then (S)-(+)-mandelic acid (4.84 g, 31.8 mmol) in isopropanol (375 mL) was added dropwise to the amine solution over 35 minutes. The reaction mixture was allowed to cool to about 72° C. and solid precipitation was observed. The slurry was cooled to room temperature and stirred for 1 hour. The solid product was collected by filtration. The wet cake was washed with isopropanol (100 mL) and dried on the filter under suction for 1 hour to give the product (S)-1-(6-bromo-3-methyl-5-oxo-5H-thiazolo[3,2-a]pyrimidin-7-yl)ethanaminium (S)-2-hydroxy-2-phenylacetate (11.9 g) as a white solid. Chiral HPLC analysis was performed on a Lux Cellulose-2, 4.6×250 mm, 5 micron column using 60% ethanol/40% hexanes as the mobile phase at a flow rate of 1 mL/min. The major enantiomer eluted at retention time 11.21 min (99.0 area %). The minor enantiomer eluted at retention time 14.31 minutes (0.96 area %). The e.e. of the desired product was 98.08%.

The product at 98.08% e.e. (11.9 g) was suspended in isopropanol (750 mL) and heated under reflux for 30 minutes. The slurry was cooled to room temperature with stirring. The solid was collected by filtration. The wet solid was washed with isopropanol (100 mL) and dried on the filter under suction for 18 hours to give 10.9 g of white solid. Chiral HPLC by the method described above gave e.e. of 98.48%.

The product at 98.48% e.e. (10.9 g) was stirred in a solution of sodium carbonate (3.9 g, 37 mmol) in water (100 mL) at room temperature for 30 minutes. The solid free base was collected by filtration, washed with water (20 mL) and dried on the filter under suction for 2 hours to give a slightly wet cake (13 g). The wet solid was dissolved in isopropanol (325 mL) at reflux and a solution of (S)-(+)-mandelic acid (3.613 g, 23.75 mmol) in isopropanol (325 mL) was added dropwise over 20 minutes to the free base solution. The solution was cooled to room temperature with stirring. The solid product was collected by filtration, washed with isopropanol (100 mL) and dried on the filter under suction for 48 hours to give pure product (S)-1-(6-bromo-3-methyl-5-oxo-5H-thiazolo[3,2-a]pyrimidin-7-yl)ethanaminium (S)-2-hydroxy-2-phenylacetate (8.4 g, 19.08 mmol, 29.3% yield) as a white solid. The e.e. of this sample was determined to be 100% as no minor enantiomer (retention time =14.31 minutes) was detected. LCMS calculated for $C_9H_{11}BrN_3OS$ $(M+H)^+$ for the free base: m/z 289.97, 287.97; Found: 289.75, 287.75. $^1$H NMR (400 MHz, DMSO-$d_6$) δ 7.33 (d, J=7.5 Hz, 2H), 7.22 (dd, J=7.1, 7.5 Hz, 2H), 7.16 (m, 2H), 4.61 (s, 1H), 4.47 (q, J=6.9 Hz, 1H), 2.68 (d, J=1.1 Hz, 3H), 1.31 (d, J=6.8 Hz, 3H).

In order to determine the absolute stereochemistry of the product, a sample was sublimed at about 105° C. to provide colorless needles suitable for X-ray crystal structure analysis. The study determined the absolute configuration of the amine bearing carbon (C-8) is S (see US 2011/0015212).

Step 6. (S)-tert-Butyl 1-(6-(3-fluorophenyl)-3-methyl-5-oxo-5H-thiazolo[3,2-a]pyrimidin-7-yl)ethylcarbamate

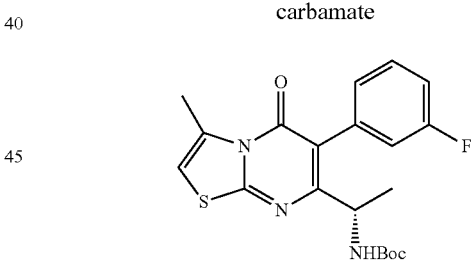

(S)-1-(6-Bromo-3-methyl-5-oxo-5H-thiazolo[3,2-a]pyrimidin-7-yl)ethanaminium (S)-2-hydroxy-2-phenylacetate (4.93 g, 11.2 mmol) was dissolved in THF (100 mL) and water (33 mL). Di-t-butyldicarbonate (3.03 g, 13.9 mmol) was added, followed by sodium bicarbonate (1.88 g, 22.4 mmol). The reaction mixture was stirred at room temperature for 30 minutes at which point the HPLC showed the reaction was near complete. Additional di-t-butyldicarbonate (0.49 g, 2.24 mmol) was then added and the reaction mixture was stirred at room temperature for 1 hour. The reaction was shown to be complete by HPLC. The reaction mixture was diluted with water (100 mL) and extracted with ethyl acetate (2×100 mL). The ethyl acetate solution was concentrated to give (S)-tent-butyl 1-(6-bromo-3-methyl-5-oxo-5H-thiazolo[3,2-a]pyrimidin-7-yl)ethylcarbamate (5.46 g, 14.1 mmol, 126% yield) which was used in the subsequent Suzuki coupling reaction without further purification.

(S)-tert-Butyl 1-(6-bromo-3-methyl-5-oxo-5H-thiazolo[3,2-a]pyrimidin-7-yl)ethylcarbamate (5.46 g, 14.1 mmol) and (3-fluorophenyl)boronic acid (2.95 g, 21.1 mmol) were suspected in 1,4-dioxane (110 mL). A solution of sodium carbonate (4.47g, 42.2 mmol) in water (27 mL) was added to the mixture followed by tetrakis(triphenylphosphine)palladium (0) catalyst (0.81 g, 0.70 mmol). The reaction mixture was degassed and heated under nitrogen at 100° C. for 16 h. HPLC indicated the starting material was consumed. The reaction mixture was cooled to room temperature and water (100 mL) was added. The resultant mixture was extracted with ethyl acetate (2×100 mL). The ethyl acetate solution was washed with saturated aqueous sodium bicarbonate (100 mL), dried over anhydrous sodium sulfate, filtered, and concentrated under reduced pressure to give a residue. The residue was purified by flash column chromatography on silica gel using 1-50% ethyl acetate in hexane as eluent to give (S)-tert-butyl 1-(6-(3-fluorophenyl)-3-methyl-5-oxo-5H-thiazolo[3,2-a]pyrimidin-7-yl)ethylcarbamate (4.34 g, 10.8 mmol, 76%) as an off-white solid. LCMS calculated for $C_{20}H_{23}FN_3O_3S$ (M+H)$^+$: m/z 404.1; Found 404.1. $^1$H NMR (500 MHz, DMSO-$d_6$) δ 7.48 (ddd, J=8.1, 7.8, 6.2 Hz, 1H), 7.18 (m, 3H), 7.05 (q, J=1.3 Hz, 1H), 6.96 (d, J=7.5 Hz, 1H), 4.41 (m, 1H), 2.66 (d, J=1.3 Hz, 3H), 1.33 (s, 9H), 1.13 (d, J=6.8 Hz, 3H).

Step 7. (S)-7-(1-Aminoethyl)-6-(3-fluorophenyl)-3-methyl-5H-thiazolo[3,2-a]pyrimidin-5-one

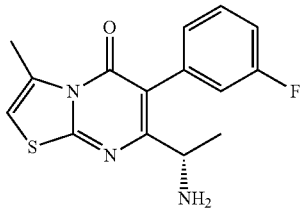 [SMILES: Cc1csc2nc([C@H](C)N)c(-c3cccc(F)c3)c(=O)n12]

(S)-tert-Butyl 1-(6-(3-fluorophenyl)-3-methyl-5-oxo-5H-thiazolo[3,2-a]pyrimidin-7-yl)ethylcarbamate (4.15 g, 10.3 mmol) was dissolved in a 4.0 M solution of hydrogen chloride in 1,4-dioxane (25.7 mL, 102.8 mmol) and the solution was stirred at room temperature for 45 minutes. HPLC indicated that the reaction was complete. To the solution was added water (10 mL) followed by 3 N aqueous sodium hydroxide solution at 0-5° C. to adjust the pH to 10. The aqueous mixture was extracted with ethyl acetate (2×30 mL). The ethyl acetate solution was dried over anhydrous sodium sulfate, filtered, and concentrated under reduced pressure to give (S)-7-(1-Aminoethyl)-6-(3-fluorophenyl)-3-methyl-5H-thiazolo[3,2-a]pyrimidin-5-one (3.30 g, 10.88 mmol, 103% yield). LCMS calculated for $C_{15}H_{15}FN_3OS$ (M+H)$^+$: m/z 304.08; Found 303.9. $^1$H NMR (400 MHz, DMSO-$d_6$) δ 8 7.45 (ddd, J=8.1, 7.9, 5.9 Hz, 1H), 7.19 (m, 1H), 7.12 (m, 2H) 7.04 (q, J=1.1 Hz, 1H), 3.57 (q, J=6.6 Hz, 1H), 2.64 (d, J=1.3 Hz, 3H), 1.10 (d, J=6.7 Hz, 3H)

Step 8. 4-Amino-6-({(1S)-1-[6-(3-fluorophenyl)-3-methyl-5-oxo-5H-[1,3]thiazolo[3,2-a]pyrimidin-7-yl]ethyl}amino)pyrimidine-5-carbonitrile A mixture of 7-[(1S)-1-aminoethyl]-6-(3-fluorophenyl)-3-methyl-5H-[1,3]thiazolo[3,2-a]pyrimidin-5-one (17 mg, 0.056 mmol)(Step 7), 4-amino-6-chloropyrimidine-5-carbonitrile (9.5 mg, 0.062 mmol) and N,N-diisopropylethylamine (0.029 mL, 0.17 mmol) in 1-butanol (0.56 mL) was heated at 120° C. for 3 h. The reaction mixture was cooled, filtered and purified on prep-LCMS (XBridge C18 Column, eluting with a gradient of acetonitrile/water containing 0.05% TFA) to give the desired product as TFA salt. LCMS calculated for $C_{20}H_{17}FN_7OS$ (M+H)$^+$: m/z=422.1; Found: 422.1. $^1$H NMR (DMSO-$d_6$, 300 MHz) δ 8.00 (1H, s), 7.58 (2H, br s), 7.49~7.42 (2H, m), 7.18 (2H, m), 7.15 (1H, s), 7.09 (1H, d, J=1.2 Hz), 4.99 (1H, m), 2.64 (3H, s), 1.27 (3H, d, J=6.9 Hz) ppm.

Example A1

PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5)P3 Detector Protein, was purchased from Echelon Biosciences (Salt Lake City, Utah). AlphaScreen™ GST Detection Kit including donor and acceptor beads was purchased from PerkinElmer Life Sciences (Waltham, Mass.). PI3Kδ (p110δ/p85α) was purchased from Millipore (Bedford, Mass.). ATP, $MgCl_2$, DTT, EDTA, HEPES and CHAPS were purchased from Sigma-Aldrich (St. Louis, Mo.).

AlphaScreen™ Assay for PI3Kδ

The kinase reaction was conducted in 384-well REMP plate from Thermo Fisher Scientific in a final volume of 40 µL. Inhibitors were first diluted serially in DMSO and added to the plate wells before the addition of other reaction components. The final concentration of DMSO in the assay was 2%. The PI3K assays were carried out at room temperature in 50 mM HEPES, pH 7.4, 5 mM $MgCl_2$, 50 mM NaCl, 5 mM DTT and CHAPS 0.04%. Reactions were initiated by the addition of ATP, the final reaction mixture consisted of 20 µM PIP2, 20 µM ATP, 1.2 nM PI3K6 were incubated for 20 min. 10 µL, of reaction mixture was then transferred to 5 µL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 L AlphaScreen™ donor and acceptor beads suspended in quench buffer containing 25 nM PI(3,4,5)P3 detector protein. The final concentration of both donor and acceptor beads is 20 mg/ml. After plate sealing, the plate was incubated in a dark location at room temperature for 2 hours. The activity of the product was determined on Fusion-alpha microplate reader (Perkin-Elmer). $IC_{50}$ determination was performed by fitting the curve of percent control activity versus the log of the inhibitor concentration using the GraphPad Prism 3.0 software.

Example A2

PI3K Enzyme Assay

Materials: Lipid kinase substrate, phosphoinositol-4,5-bisphosphate (PIP2), was purchased from Echelon Biosciences (Salt Lake City, Utah). PI3K isoforms α, β, δ and γ were purchased from Millipore (Bedford, Mass.). ATP, $MgCl_2$, DTT, EDTA, MOPS and CHAPS were purchased from Sigma-Aldrich (St. Louis, Mo.).

The kinase reaction was conducted in clear-bottom 96-well plate from Thermo Fisher Scientific in a final volume of 24 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM $MgCl_2$, 5 mM DTT and CHAPS 0.03%. The reaction mixture was prepared containing 50 µM PIP2, kinase and varying concentration of inhibitors. Reactions were initiated by the addition of ATP containing 2.2 µCi [γ-$^{33}$P]ATP to a final concentration of 1000 µM. The final concentration of PI3K isoforms α, β, δ and γ in the assay were 1.3, 9.4, 2.9 and 10.8 nM respectively. Reactions were incubated for 180 min and terminated by the addition of 100 µL of 1 M potassium phosphate pH 8.0, 30 mM EDTA quench buffer. A 100 µL aliquot of the reaction solution was then transferred to 96-well Millipore MultiScreen IP 0.45 µm PVDF filter plate (The filter plate was prewetted with 200 µL 100% ethanol, distilled water, and 1 M potassium phosphate pH 8.0, respectively). The filter plate was aspirated on a Millipore Manifold under vacuum and washed with 18×200 µL wash buffer containing 1 M potassium phosphate pH 8.0 and 1 mM ATP. After drying by aspiration and blotting, the plate was air dried in an incubator at 37° C. overnight. Packard TopCount adapter (Millipore) was then attached to the plate followed with addition of 120 µL Microscint 20 scintillation cocktail (Perkin Elmer) in each well. After the plate sealing, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software.

Example A3

PI3Kδ Scintillation Proximity Assay

Materials

[γ-$^{33}$P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 µM PIP2, 20 µM ATP, 0.2 µCi [γ-$^{33}$P] ATP, 4 nM PI3Kδ. Reactions were incubated for 210 min and terminated by the addition of 40 µL SPA beads suspended in quench buffer: 150 mM potassium phosphate pH 8.0, 20% glycerol. 25 mM EDTA, 400 µM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. Data for Examples 1 and 2 is presented in Table 1 below.

TABLE 1

| IC$_{50}$ data for enzyme assay | |
|---|---|
| Example | IC$_{50}$ (nM) |
| 1 | <20 |
| 2 | <20 |

Example B

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells (2×10$^5$/well/200 µL) are cultured in 96-well ultra-low binding plates (Corning, Corning, N.Y.) in RPMI1640, 10% FBS and goat F(ab')2 anti-human IgM (10 µg/ml) (Invitrogen, Carlsbad, Calif.) in the presence of different amount of test compounds for three days. [$^3$H]-thymidine (1 µCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience).

Example C

Pfeiffer Cell Proliferation Assay

Pfeiffer cell line (diffuse large B cell lymphoma) was purchased from ATCC (Manassas, Va.) and maintained in the culture medium recommended (RPMI and 10% FBS). To measure the anti-proliferation activity of the compounds, the Pfeiffer cells were plated with the culture medium (2×10$^3$ cells/well/per 200 µl) into 96-well ultra-low binding plates (Corning, Corning, N.Y.), in the presence or absence of a concentration range of test compounds. After 3-4 days, [$^3$H]-thymidine (1 µCi/well) (PerkinElmer, Boston, Mass.) in PBS wass then added to the cell culture for an additional 12 hours before the incorporated radioactivity was separated by filtration with water through GF/B filters (Packard Bioscience, Meridenj, Conn.) and measured by liquid scintillation counting with a TopCount (Packard Bioscience). Table 2 shows Pfeiffer cell proliferation data for certain compounds described herein.

TABLE 2

| IC$_{50}$ data for Pfeiffer cell proliferation assay | |
|---|---|
| Example | IC$_{50}$ (nM) |
| 1 | <20 |
| 2 | <20 |

Example C

Akt Phosphorylation Assay

Ramos cells (B lymphocyte from Burkitts lymphoma) are obtained from ATCC (Manassas, Va.) and maintained in RPMI1640 and 10% FBS. The cells ($3\times10^7$ cells /tube/3 mL in RPMI) are incubated with different amounts of test compounds for 2 hrs at 37° C. and then stimulated with goat F(ab')2 anti-human IgM (5 µg/mL) (Invitrogen) for 17 minutes in a 37° C. water bath. The stimulated cells are spun down at 4° C. with centrifugation and whole cell extracts are prepared using 300 µL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

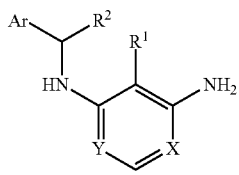

I or a pharmaceutically acceptable salt thereof; wherein:
X is CH or N;
Y is CH or N;
provided that at least one of X and Y is N;
Ar is

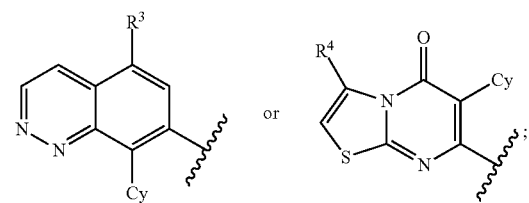

$R^1$ is F, CN, $C_{1-3}$ haloalkyl, $C_{1-4}$ alkyl-NHC(=O)— or $(C_{1-4}$ alkyl$)_2$NC(=O)—;
$R^2$ is methyl or ethyl;
$R^3$ is F, Cl, or methyl;
$R^4$ is Cl or methyl; and
Cy is phenyl or pyridyl, each of which is substituted by 0, 1, or 2 groups independently selected from fluoro and chloro groups.

2. The compound of claim 1, or a pharmaceutically acceptable salt thereof, wherein:
X is N and Y is N.

3. The compound of claim 1, or a pharmaceutically acceptable salt thereof, wherein $R^1$ is CN.

4. The compound of claim 1, or a pharmaceutically acceptable salt thereof, wherein $R^2$ is methyl.

5. The compound of claim 1, or a pharmaceutically acceptable salt thereof, wherein Cy is phenyl or pyridyl, each of which is substituted by 0, 1, or 2 fluoro groups.

6. The compound of claim 1, or a pharmaceutically acceptable salt thereof, wherein Cy is phenyl, which is substituted by 0, 1, or 2 fluoro groups.

7. The compound of claim 1, or a pharmaceutically acceptable salt thereof, wherein Cy is phenyl.

8. The compound of claim 1, or a pharmaceutically acceptable salt thereof, wherein Cy is 3-fluorophenyl.

9. The compound of claim 1, or a pharmaceutically acceptable salt thereof, wherein Cy is 2-fluorophenyl.

10. The compound of claim 1, or a pharmaceutically acceptable salt thereof, wherein Cy is 3,5-difluorophenyl.

11. The compound of claim 1, or a pharmaceutically acceptable salt thereof, wherein Cy is pyridyl, which is substituted by 0 or 1 fluoro groups.

12. The compound of claim 1, or a pharmaceutically acceptable salt thereof, wherein Ar is

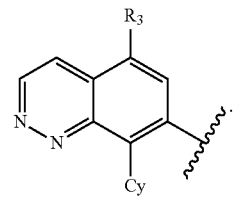

13. The compound of claim 1, or a pharmaceutically acceptable salt thereof, wherein Ar is

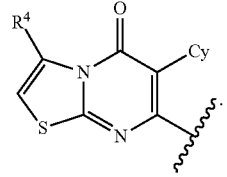

14. The compound of claim 1, or a pharmaceutically acceptable salt thereof, wherein $R^3$ is Cl or methyl.

15. The compound of claim 1, or a pharmaceutically acceptable salt thereof, wherein $R^3$ is Cl.

16. The compound of claim 1, or a pharmaceutically acceptable salt thereof, wherein $R^3$ is methyl.

17. The compound of claim 1, or a pharmaceutically acceptable salt thereof, wherein $R^4$ is methyl.

18. The compound of claim 1, wherein the compound is a compound of Formula II:

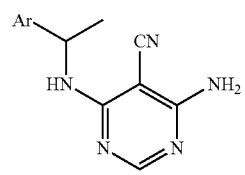

II or a pharmaceutically acceptable salt thereof, wherein:
Ar is:

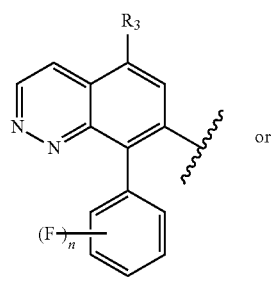

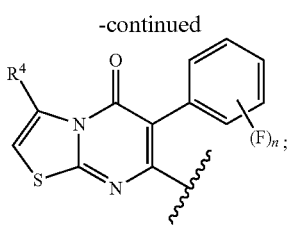

n is 0, 1, or 2;
$R^3$ is F, Cl, or methyl; and
$R^4$ is Cl or methyl.

19. The compound according to claim 1 which is 4-amino-6-({1-[5-chloro-8-(3-fluorophenyl)cinnolin-7-yl]ethyl}amino)-pyrimidine-5-carbonitrile or a pharmaceutically acceptable salt thereof.

20. The compound according to claim 1 which is 4-amino-6-({(1S)-1-[5-chloro-8-(3-fluorophenyl)cinnolin-7-yl]ethyl}amino)-pyrimidine-5-carbonitrile or a pharmaceutically acceptable salt thereof.

21. The compound according to claim 1 which is 4-amino-6-({1-[6-(3-fluorophenyl)-3-methyl-5-oxo-5H-[1,3]thiazolo[3,2-a]pyrimidin-7-yl] ethyl}amino)pyrimidine-5-carbonitrile or a pharmaceutically acceptable salt thereof.

22. The compound according to claim 1 which is 4-amino-6-({(1S)-1-[6-(3-fluorophenyl)-3-methyl-5-oxo-5H-[1,3]thiazolo[3,2-a]pyrimidin-7-yl]ethyl}amino)pyrimidine-5-carbonitrile or a pharmaceutically acceptable salt thereof.

23. A pharmaceutical composition comprising a compound according to claim 1, or a pharmaceutically acceptable salt thereof, and at least one pharmaceutically acceptable carrier.

24. A method of inhibiting an activity of a PI3K kinase, comprising contacting the kinase with a compound of claim 1, or a pharmaceutically acceptable salt thereof.

25. A method of treating a disease in a human patient, wherein said disease is osteoarthritis, restenosis, atherosclerosis, arthritis, diabetic retinopathy, psoriasis, inflammation, pancreatitis, inflammatory bowel disease, myasthenia gravis, multiple sclerosis, or Sjöogren's syndrome, comprising administering to said human patient a therapeutically effective amount of a compound of claim 1, or a pharmaceutically acceptable salt thereof.

26. A method of treating an immune-based disease in a human patient, wherein said immune-based disease is rheumatoid arthritis, allergy, asthma, glomerulonephritis, lupus, or inflammation related to any of the aforementioned, comprising administering to said human patient a therapeutically effective amount of a compound of claim 1, or a pharmaceutically acceptable salt thereof.

27. A method of treating a cancer in a human patient, wherein said cancer is breast, prostate, colon, endometrial, brain, bladder, skin, uterus, ovary, lung, pancreatic, renal, gastric, or a hematological cancer, comprising administering to said human patient a therapeutically effective amount of a compound of claim 1, or a pharmaceutically acceptable salt thereof.

28. The method of claim 27, wherein said hematological cancer is acute myeloblastic leukemia, chronic myeloid leukemia, or B cell lymphoma.

29. A method of treating a lung disease in a human patient, wherein said lung disease is acute lung injury (ALI) or adult respiratory distress syndrome (ARDS), comprising administering to said human patient a therapeutically effective amount of a compound of claim 1 or a pharmaceutically acceptable salt thereof.

30. The method of claim 24, wherein said PI3K kinase is PI3Kδ.

31. The method of claim 27, wherein said hematological cancer is B cell lymphoma.

32. The method of claim 27, wherein said hematological cancer is diffuse large B cell lymphoma.

* * * * *